US009134202B2

(12) United States Patent
Bruehwiler et al.

(10) Patent No.: US 9,134,202 B2
(45) Date of Patent: Sep. 15, 2015

(54) ROBOTIC END EFFECTOR FOR FROZEN ALIQUOTTER AND METHODS OF TAKING A FROZEN ALIQUOT FROM BIOLOGICAL SAMPLES

(75) Inventors: Michel Bruehwiler, Newton, MA (US); Saeed Sokhanvar, Cambridge, MA (US); Cole Constantineau, Cambridge, MA (US); Melissa Rosen, Lynn, MA (US); Todd Basque, Arlington, VA (US)

(73) Assignee: CryoXtract Instruments, LLC, Arlington, VA (US)

( * ) Notice: Subject to any disclaimer, the term of this patent is extended or adjusted under 35 U.S.C. 154(b) by 540 days.

(21) Appl. No.: 13/359,301

(22) Filed: Jan. 26, 2012

(65) Prior Publication Data

US 2013/0192391 A1 Aug. 1, 2013

(51) Int. Cl.

| | |
|---|---|
| ***G01N 1/08*** | (2006.01) |
| ***G01F 17/00*** | (2006.01) |
| ***G01N 1/42*** | (2006.01) |
| ***G01N 35/00*** | (2006.01) |
| *G01N 35/10* | (2006.01) |

(52) U.S. Cl.

CPC *G01N 1/08* (2013.01); *G01F 17/00* (2013.01); *G01N 1/42* (2013.01); *G01N 35/0099* (2013.01); *G01N 35/10* (2013.01); *G01N 2035/1025* (2013.01)

(58) Field of Classification Search

CPC .................................. G01F 17/00; G01N 1/08

See application file for complete search history.

(56) References Cited

U.S. PATENT DOCUMENTS

| | | | |
|---|---|---|---|
| 6,103,518 | A | 8/2000 | Leighton |
| 6,468,783 | B1 | 10/2002 | Leighton |
| 6,534,307 | B1 | 3/2003 | Muraca |
| 6,582,967 | B2 | 6/2003 | Muraca |
| 7,572,410 | B2 | 8/2009 | Chaumat |
| 7,682,572 | B2 | 3/2010 | Postoyalko et al. |
| 2002/0127631 | A1 | 9/2002 | Schiller et al. |
| 2002/0177119 | A1 | 11/2002 | Wisniewski |

(Continued)

FOREIGN PATENT DOCUMENTS

| | | |
|---|---|---|
| WO | 2007084483 | 7/2007 |
| WO | 2012074771 | 6/2012 |

OTHER PUBLICATIONS

Lashmar, et al., "Bulk Freeze-Thawing of Macromolecules Effect of Cryoconcentration on their Formulation and Stability", BioProcess International, Jun. 2007, 8 pages.

Maity et al., "Mapping of solution components, pH changes, protein stability and the elimination of protein precipitation during freeze-thawing of fibroblast growth factor 20", Inter. Journal of Pharm., 378, 2009, pp. 122-135.

(Continued)

*Primary Examiner* — Paul West

(74) *Attorney, Agent, or Firm* — Senniger Powers LLP

(57) ABSTRACT

A robotic end effector for collecting frozen aliquots from an array of frozen samples in a plurality of containers has a coring bit for taking frozen sample cores from the frozen samples and a frozen sample core extraction system adapted to extract frozen sample cores from the frozen samples. A fill level detection system is adapted to detect the positions of the surfaces of the frozen samples. A processor is adapted to receive signals from the fill level detection system and use the signals and information concerning operation of the frozen sample core extraction system to determine at least one of the following: (a) the amount of material contained in a frozen sample core obtained by the coring bit; and (b) the number of frozen sample cores needed from a particular frozen sample to obtain a predetermined amount of material from that frozen sample.

24 Claims, 25 Drawing Sheets

(56) References Cited

U.S. PATENT DOCUMENTS

| | | | |
|---|---|---|---|
| 2003/0026732 | A1 | 2/2003 | Gordon et al. |
| 2006/0199169 | A1 | 9/2006 | Lam et al. |
| 2009/0019877 | A1 | 1/2009 | Larson et al. |
| 2009/0181463 | A1 | 7/2009 | Chen |
| 2010/0152895 | A1 | 6/2010 | Dai |
| 2010/0217431 | A1 | 8/2010 | Tribble et al. |
| 2010/0294046 | A1 | 11/2010 | Boeke et al. |

OTHER PUBLICATIONS

Webb, et al., "Freezing Bulk-Scale Biopharmaceuticals Using Common Techniques-and the Magnitude of Freeze-Concentration", BioPharm, vol. 15, No. 5 , May 2002, pp. 1-8.

International Search Report regarding corresponding PCT/US2013/023453, dated May 15, 2013, 4 pages.

Written Opinion regarding corresponding PCT/US2013/023453, dated May 15, 2013, 7 pages.

ROBOTIC END EFFECTOR FOR FROZEN ALIQUOTTER AND METHODS OF TAKING A FROZEN ALIQUOT FROM BIOLOGICAL SAMPLES

FIELD OF INVENTION

The present invention relates generally to apparatus and methods for taking frozen aliquots from a frozen biological samples while maintaining integrity of the samples, and more particularly to apparatus and methods for ensuring a frozen aliquot taken from a frozen sample is suitable material for analysis.

BACKGROUND

Biological samples are commonly preserved to support a broad variety of biomedical and biological research that includes but is not limited to translational research, molecular medicine, and biomarker discovery. Biological samples include any samples which are of animal (including human), plant, protozoal, fungal, bacterial, viral, or other biological origin. For example, biological samples include, but are not limited to, organisms and/or biological fluids isolated from or excreted by an organism such as plasma, serum, urine, whole blood, cord blood, other blood-based derivatives, cerebral spinal fluid, mucus (from respiratory tract, cervical), ascites, saliva, amniotic fluid, seminal fluid, tears, sweat, any fluids from plants (including sap); cells (e.g., animal, plant, protozoal, fungal, or bacterial cells, including buffy coat cells; cell lysates, homogenates, or suspensions; microsomes; cellular organelles (e.g., mitochondria); nucleic acids (e.g., RNA, DNA), including chromosomal DNA, mitochondrial DNA, and plasmids (e.g., seed plasmids); small molecule compounds in suspension or solution (e.g. small molecule compounds in DMSO); and other fluid-based biological samples. Biological samples may also include plants, portions of plants (e.g., seeds) and tissues (e.g., muscle, fat, skin, etc.).

Biobanks typically store these valuable samples in containers (e.g., tubes, vials, or the like) and cryopreserve them (e.g., in freezers at −80 degrees centigrade, or lower using liquid Nitrogen or the vapor phase above liquid Nitrogen) to preserve the biochemical composition and integrity of the frozen sample as close as possible to the in vivo state to facilitate accurate, reproducible analyses of the samples.

From time to time, it may be desirable to run one or more tests on a sample that has been frozen. For example, a researcher may want to perform tests on a set of samples having certain characteristics. A particular sample may contain enough material to support a number of different tests. In order to conserve resources, smaller samples known as aliquots are commonly taken from larger cryopreserved samples (which are sometimes referred to as parent samples) for use in one or more tests so the remainder of the parent sample will be available for one or more different future tests.

Biobanks have adopted different ways to address this need to provide sample aliquots. One option is to freeze a sample in large volume, thaw it when aliquots are requested and then refreeze any remainder of the parent sample for storage in the cryopreserved state until future aliquots are needed. This option makes efficient use of frozen storage space; yet this efficiency comes at the cost of sample quality. Exposing a sample repeatedly to freeze/thaw cycles can degrade the sample's critical biological molecules (e.g., RNA) and damage biomarkers, either of which could compromise the results of any study using data obtained from the damaged samples.

Another option is to freeze a sample in large volume, thaw it when an aliquot is requested, subdivide the remainder of the parent sample in small volumes to make additional aliquots for future tests and then refreeze these smaller volume aliquots to cryopreserve each aliquot separately until needed for a future test. This approach limits the number of freeze/thaw cycles to which a sample is exposed, but there is added expense associated with the larger volume of frozen storage space, labor, and larger inventory of sample containers (e.g. tubes, vials, or the like) required to maintain the cryopreserved aliquots. Moreover, the aliquots can be degraded or damaged by even a limited number freeze/thaw cycles.

Yet another approach is to divide a large volume sample into smaller volume aliquots before freezing them for the first time. This approach can limit the number of freeze thaw cycles to which a sample may be subjected to only one; yet, there are disadvantages associated with the costs of labor, frozen storage space, and sample container inventory requirements with this approach.

U.S. pre-grant publication No. 20090019877, the contents of which are hereby incorporated by reference, discloses a system for extracting frozen sample cores from a frozen biological sample without thawing the original (parent) sample. The system uses a drill including a hollow coring bit to take a frozen core sample from the original parent sample without thawing the parent sample. The frozen sample core obtained by the drill is used as the aliquot for the test. After the frozen core is removed, the remainder of the sample is returned to frozen storage in its original container until another aliquot from the parent sample is needed for a future test.

The present inventors have developed systems and methods, which will be described below, that improve the ability to provide frozen aliquots from a frozen sample using a system that extracts frozen sample cores from frozen samples without thawing the samples.

SUMMARY

One aspect of the invention is a robotic end effector for collecting frozen aliquots from an array of frozen samples, wherein the frozen samples are contained in a plurality of containers and each frozen sample has a surface spaced from a bottom of the container. The robotic end effector includes a coring bit for taking frozen sample cores from the frozen samples. A frozen sample core extraction system is adapted to move the coring bit relative to the frozen samples in a manner that extracts frozen sample cores from the frozen samples. The effector also has a fill level detection system adapted to detect the positions of the surfaces of the frozen samples. A processor is adapted to receive signals from the fill level detection system and use the signals and information concerning operation of the frozen sample core extraction system to determine at least one of the following: (a) the amount of material contained in a frozen sample core obtained by the coring bit; and (b) the number of frozen sample cores needed from a particular frozen sample to obtain a predetermined amount of material from that frozen sample.

Another aspect of the invention is a fill level detection system for a frozen aliquotter system that automatically collects frozen aliquots from an array of frozen samples, wherein the frozen samples are contained in a plurality of containers and each frozen sample has a surface spaced from a bottom of the container. The fill level detection system includes a processor and at least one of the following: (a) an imaging system and a system adapted to move the imaging system toward and away from one of the frozen samples, wherein the processor is adapted to determine when the imaging system is focused on the surface of said frozen sample and use information about the position of the imaging system when it is focused on the surface of said frozen sample to determine the position of the surface of the frozen sample; (b) a probe, a system for moving the probe toward and away from the surface of one of the frozen samples, and a sensor adapted to detect contact between the surface of said frozen sample and the probe, wherein the processor is adapted to use a signal from the sensor and information about operation of the system for moving the probe to determine the position of the surface of said frozen sample; and (c) a robotic end effector including a gripper adapted to lift one of the containers and a sensor adapted to detect a weight of the lifted container by measuring a force exerted by the lifted container on the end effector, wherein the processor is adapted to use a signal from the sensor and information about the sample contained in the container to determine the position of the surface of said frozen sample.

Yet another aspect of the invention is an automated method of taking a frozen aliquot from a frozen sample contained in a container. The method includes using a sensor to determine the position of a surface of the frozen sample that is spaced from a bottom of the container and output a signal indicative of the position of the surface to a processor. The tip of a coring bit is robotically inserted into the frozen sample under the guidance of the processor to a position within the frozen sample. The coring bit is robotically withdrawn from the frozen sample to obtain a frozen sample core, wherein the frozen sample core forming at least part of the frozen aliquot. The method includes ensuring that the frozen aliquot includes at least a predetermined minimum volume of sample material by using information about the position of the surface of the sample and said position within the frozen sample to determine whether or not the frozen aliquot contains at least the predetermined minimum volume of sample material.

Another aspect of the invention is a robotic end effector for moving and weighing containers. The robotic end effector includes a frame, mounting bracket, and a gripper assembly mounted on the mounting bracket. The gripper assembly is operable to hold a container containing a sample material in a suspended position such that the gripper assembly bears the weight of the container and sample material in the container. A weight sensor is connected to the frame and mounting bracket. The weight sensor is adapted to output a signal indicative of an amount of force transferred between the frame and mounting bracket through the weight sensor. The robotic end effector also includes a locking mechanism having a locking element. The locking element is selectively moveable between a locking position and a non-locking position. In the locking position, the locking element limits relative movement between the mounting bracket and frame and bears at least some of the weight of the mounting bracket. In the non-locking position, the locking element does not bear any of the weight of the mounting bracket and the weight sensor bears the weight of the mounting bracket.

Other objects and features will be in part apparent and in part pointed out hereinafter.

BRIEF DESCRIPTION OF THE DRAWINGS

Corresponding reference numbers indicate corresponding parts throughout the drawings.

DETAILED DESCRIPTION

Figure 1:
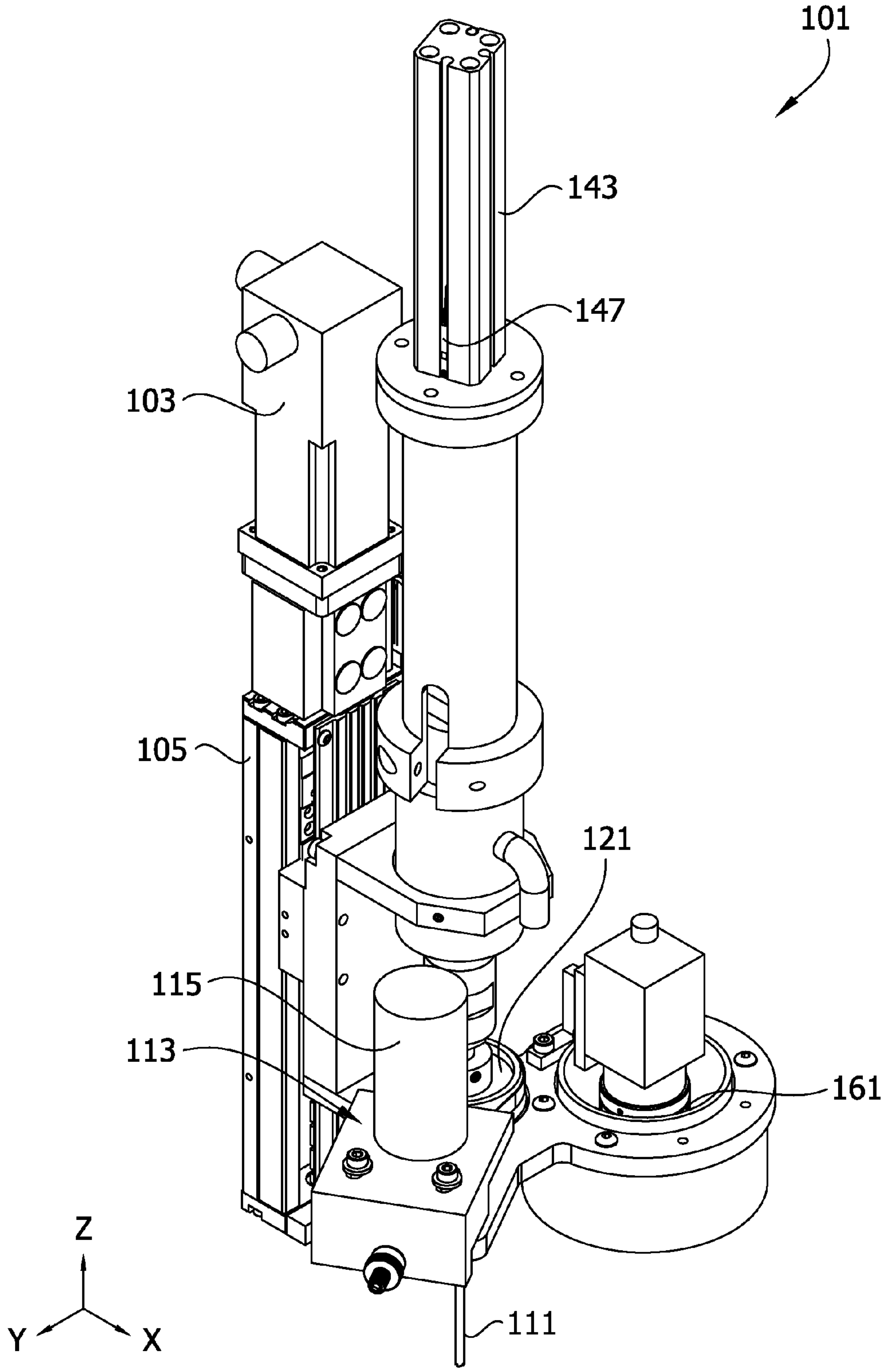
FIG. 1 is a perspective of one embodiment of a robotic end effector for taking frozen aliquots from frozen samples.
Figure 2:
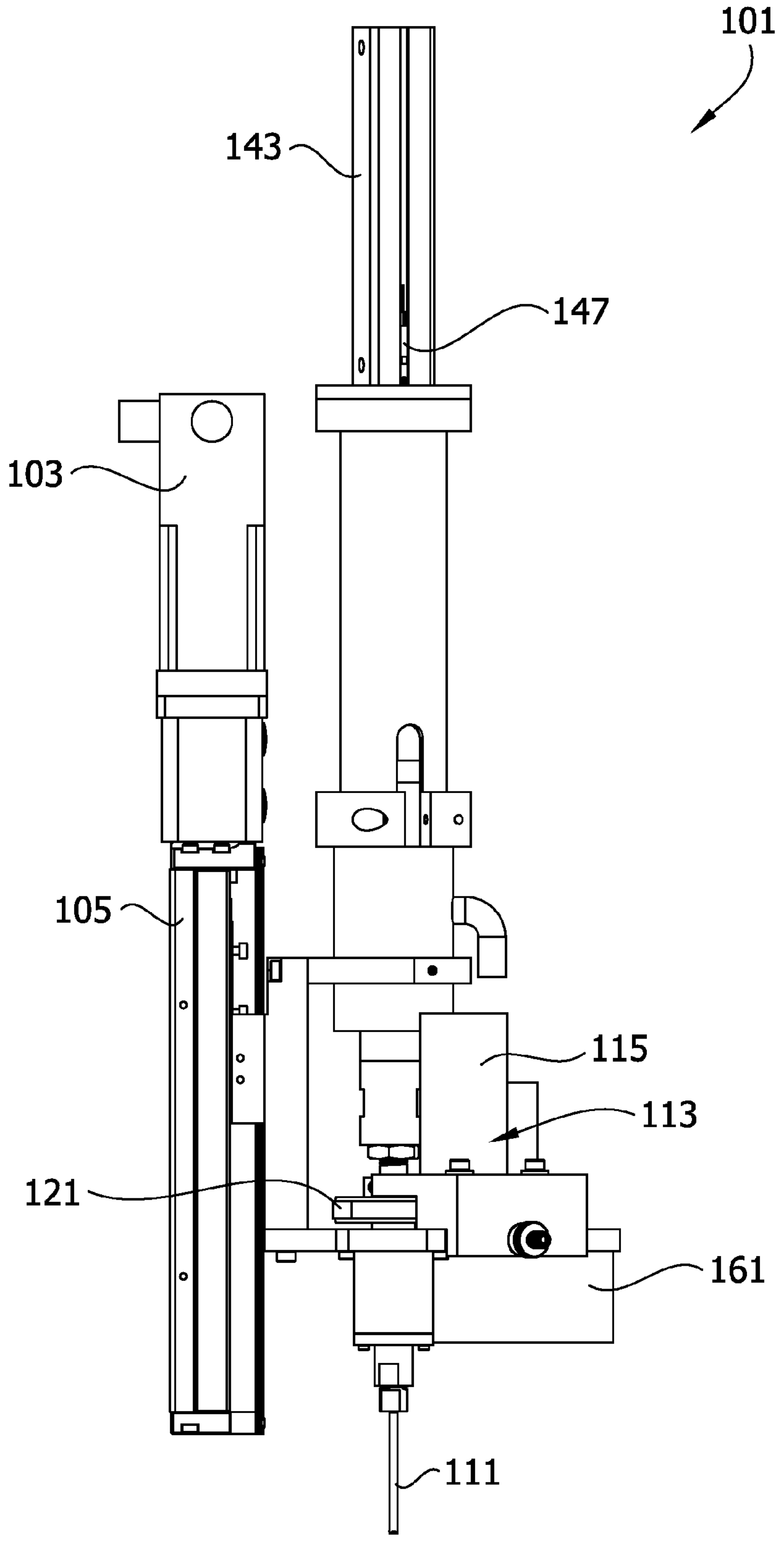
FIG. 2 is a side elevation of the robotic end effector.
Figure 3:
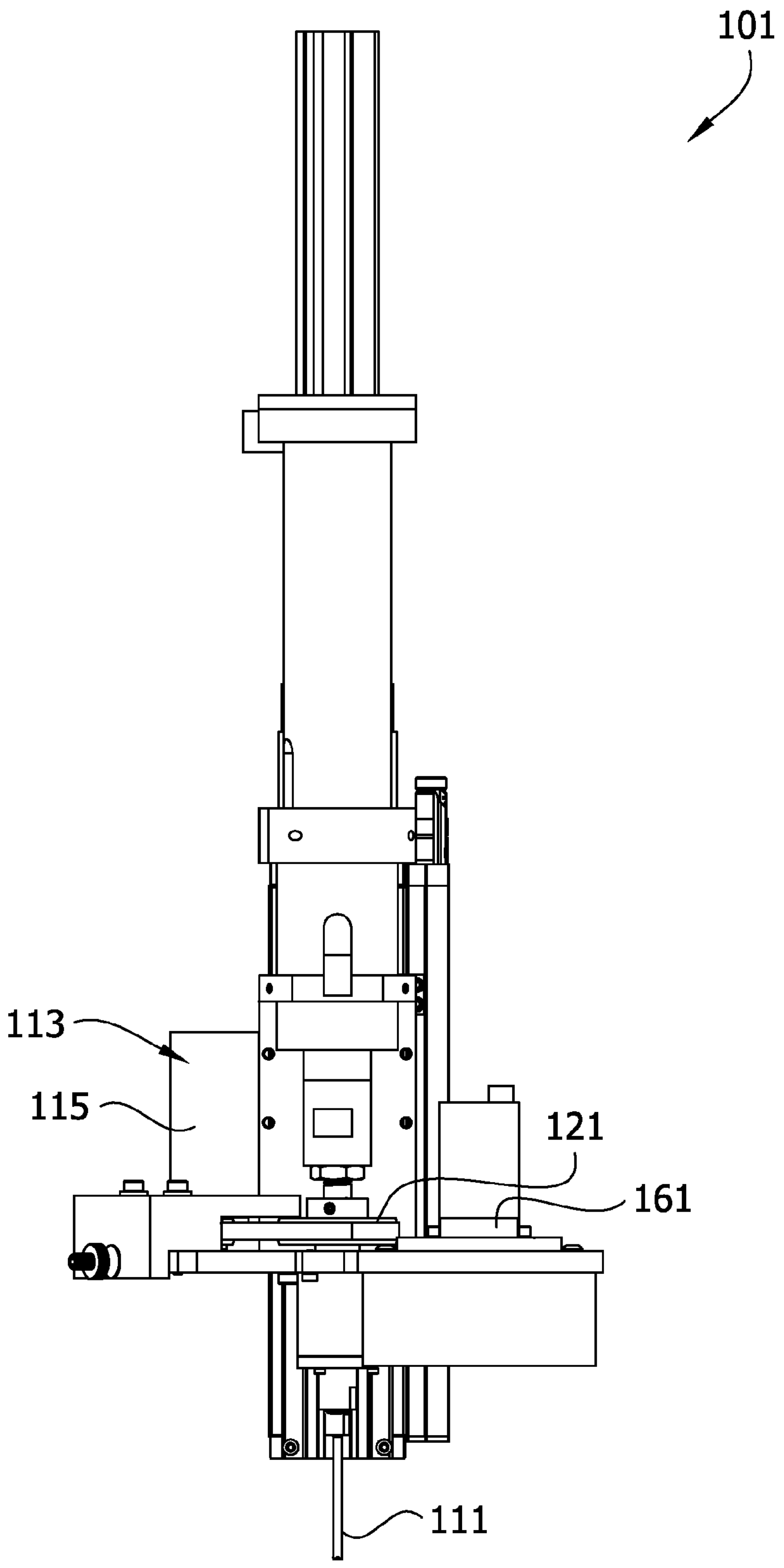
FIG. 3 is a front elevation of the robotic end effector.
Figure 4:
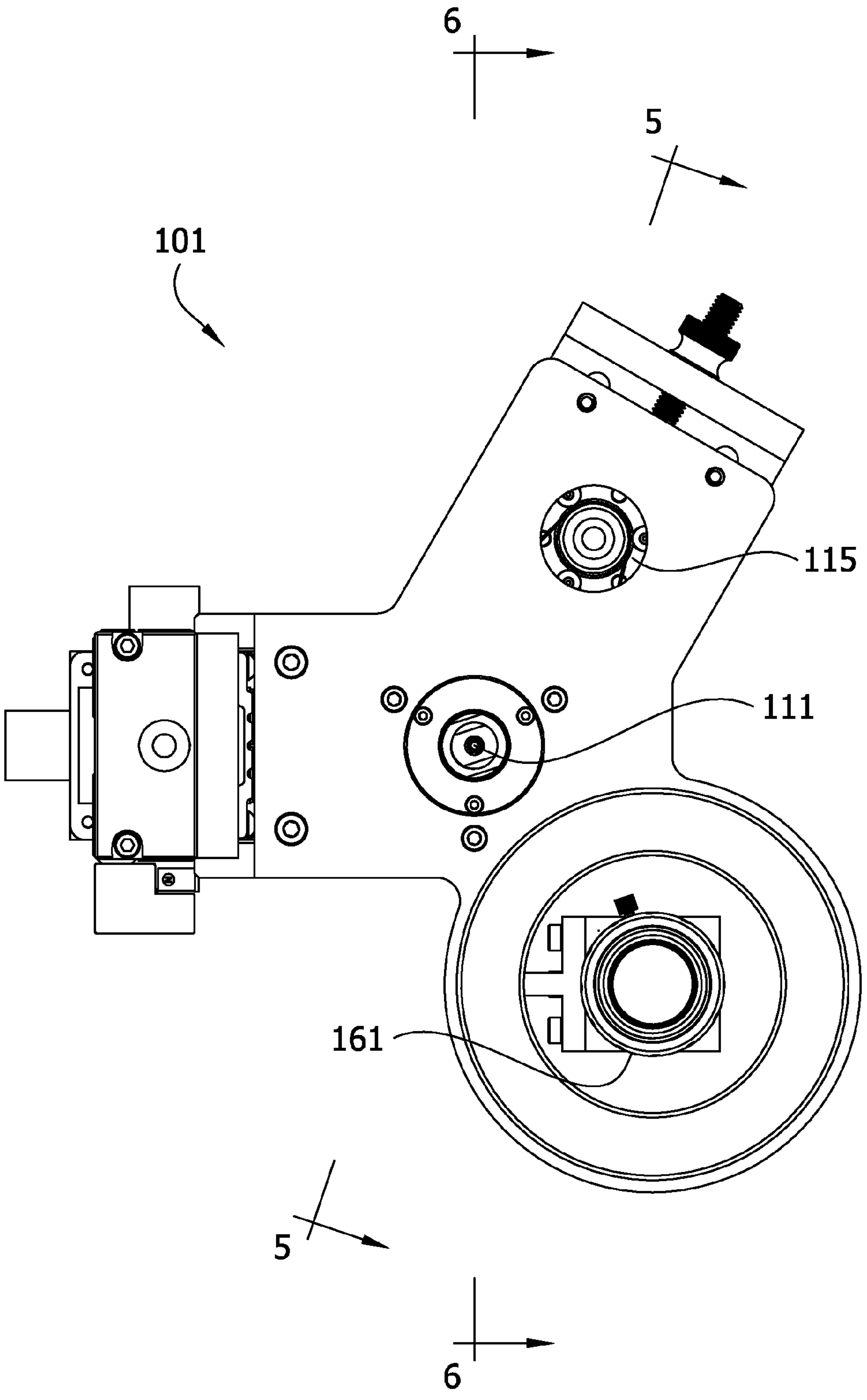
FIG. 4 is a bottom plan of the robotic end effector.

One embodiment of a robotic end effector, generally designated 101, is illustrated in FIGS. 1-8. The robotic end effector 101 is suitable for use with a robotic positioning system (not shown) to automatically collect a plurality of frozen aliquots from an array of frozen samples (e.g., cryopreserved biological samples from one or more biobanks). The end effector 101 can be adapted for use with virtually any robotic positioning system within the broad scope of the invention, including without limitation, an articulated robotic arm, a non-articulated robot arm, a gantry style or other Cartesian coordinate positioning system (whether or not such positioning system includes a robotic arm), a selectively compliant assembly robot arm (SCARA), and the like. Positioning systems that move the samples relative to the environment without moving the end effector 101 relative to the environment are also within the scope of the invention. Any robotic positioning system that is capable of automatically positioning the end effector 101 relative to the samples such that the end effector and robotic positioning system together form a robotic system capable of obtaining frozen aliquots from the frozen samples is suitable within the broad scope of the invention.

For example, the robotic end effector 101 illustrated in the drawings is suitable for use with at least a gantry style Cartesian coordinate positioning system. The end effector 101 includes a Z-axis motor 103 and Z-axis carriage 105 adapted for connection to a mount (not shown) on the frame of a gantry style robotic positioning system that is operable to provide controlled movement of the mount along the X and Y axes. When mounted on the robotic positioning system, the Z-axis carriage 105 supports the rest of the end effector 101 so the robotic positioning system can move the entire end effector by moving the Z-axis carriage. It is recognized that the end effector can be modified so some of the components and/or functionalities of the end effector are located on or performed by the positioning system and/or so some of the components and/or functionalities of the positioning system are located on or performed by the end effector without departing from the scope of the invention.

The robotic end effector 101 includes a hollow coring bit 111 (e.g., hollow needle having a cutting tip) and a frozen sample core extraction system 113 adapted to move the coring bit relative to the frozen samples to extract frozen sample cores from the frozen samples. For example, the frozen sample core extraction system 113 in the illustrated embodiment includes a motor 115 adapted to rotate the coring bit 111. The Z-axis motor 103 also constitutes part of the frozen sample core extraction system 113 in this embodiment and is operable to move the coring bit 111 along the Z-axis (e.g., vertically up and down). The end effector 101 includes a spindle 121 that holds the coring bit 111 so a long axis of the coring bit 111 is aligned with the Z-axis (e.g., so the coring bit is in a vertical orientation). The spindle 121 is mounted for rotation about the Z-axis by the coring bit motor 115 so the coring bit motor rotates the spindle to produce rotation of the coring bit 111. Thus, the frozen sample core extraction system 113 is operable to rotate the coring bit 111 while moving it axially into a frozen sample to produce a drilling action. When the drilling of the frozen sample is complete, the Z-axis motor 103 can move (e.g., raise) the coring bit 111 back out of the frozen sample so a frozen sample core is retained within the hollow coring bit. Although the robotic end effector 101 illustrated in the drawings rotates the coring bit 111, the frozen sample core extraction system may operate differently within the broad scope of the invention. Any system that can move a coring bit or other suitable sampling instrument into a frozen sample and withdraw it so a frozen sample core is retained therein can serve as the frozen sample core extraction system within the broad scope of the invention.

The robotic end effector 101 includes a fill level detection system 131 adapted to detect the positions of the surfaces (e.g., upper surfaces) of the frozen samples in the containers. Biobanks store frozen samples in containers (e.g., tubes, vials, or the like). Each frozen sample has a surface spaced from a bottom of the container that is formed when a sample was frozen or refrozen in the respective container to form the frozen sample. The position of the surface of the frozen sample within the container can vary for a number of different reasons. For example, the amount of sample initially placed in the container can vary due to differences in the amount of sample available, the lack of uniformity in the actions of workers or others who fill the containers with sample material, tilting of the container during the freezing period, a decision to not fill the container to capacity, or other reasons. Furthermore, some of the frozen samples may have been refrozen after an aliquot was previously taken from the sample while it was in a thawed state. The level of the surface of the frozen sample will be lower than it was initially when the sample is refrozen after an aliquot has been removed from the container in a thawed state. Although the sample may be oriented so the surface is an upper surface at the top of the sample, it is understood the sample and container may be oriented so the surface is not at the top of the sample within the scope of the invention (e.g., a container and sample can be rotated from an upright orientation to a horizontal orientation after the sample is frozen).

A processor (not shown) receives signals from the fill level detection system 131. The processor is suitably the same processor that controls operation of the sample core extraction system 113. The processor can also control the robotic positioning system and any other aspects of the robotic system resulting from the combination of the end effector 101 and robotic positioning system. The processor uses the signals from the fill level detection system 131 in conjunction with information about the operation of the sample core extraction system 113 to determine at least one of the following: (a) the amount of frozen sample material contained in a frozen sample core obtained by the end effector 101 (e.g., obtained by the coring bit 111); and (b) the number of frozen sample cores needed from a particular frozen sample to obtain a predetermined amount of sample material from that frozen sample. It is sometimes necessary for a sample aliquot provided for a particular test to contain at least a predetermined minimum amount of sample material. For example, some tests require at least about 100 μL of sample material. The fill level detection system 131 enables the processor to determine how much sample material is contained in a frozen sample and use this information to determine how many frozen sample cores are needed to provide the predetermined minimum amount of sample material in the aliquot while conserving valuable sample material for use in future tests.

The fill level detection system 131 in the illustrated embodiment identifies the position of the surface of a frozen sample by detecting contact between the frozen sample and the end effector 101 as the end effector is moved toward the sample. When contact is detected, the processor receives a signal indicating contact has been detected. The processor uses information about the position of the end effector 101 corresponding to the time when the end effector contacted the sample to assess the location of the sample surface.

Figure 5:
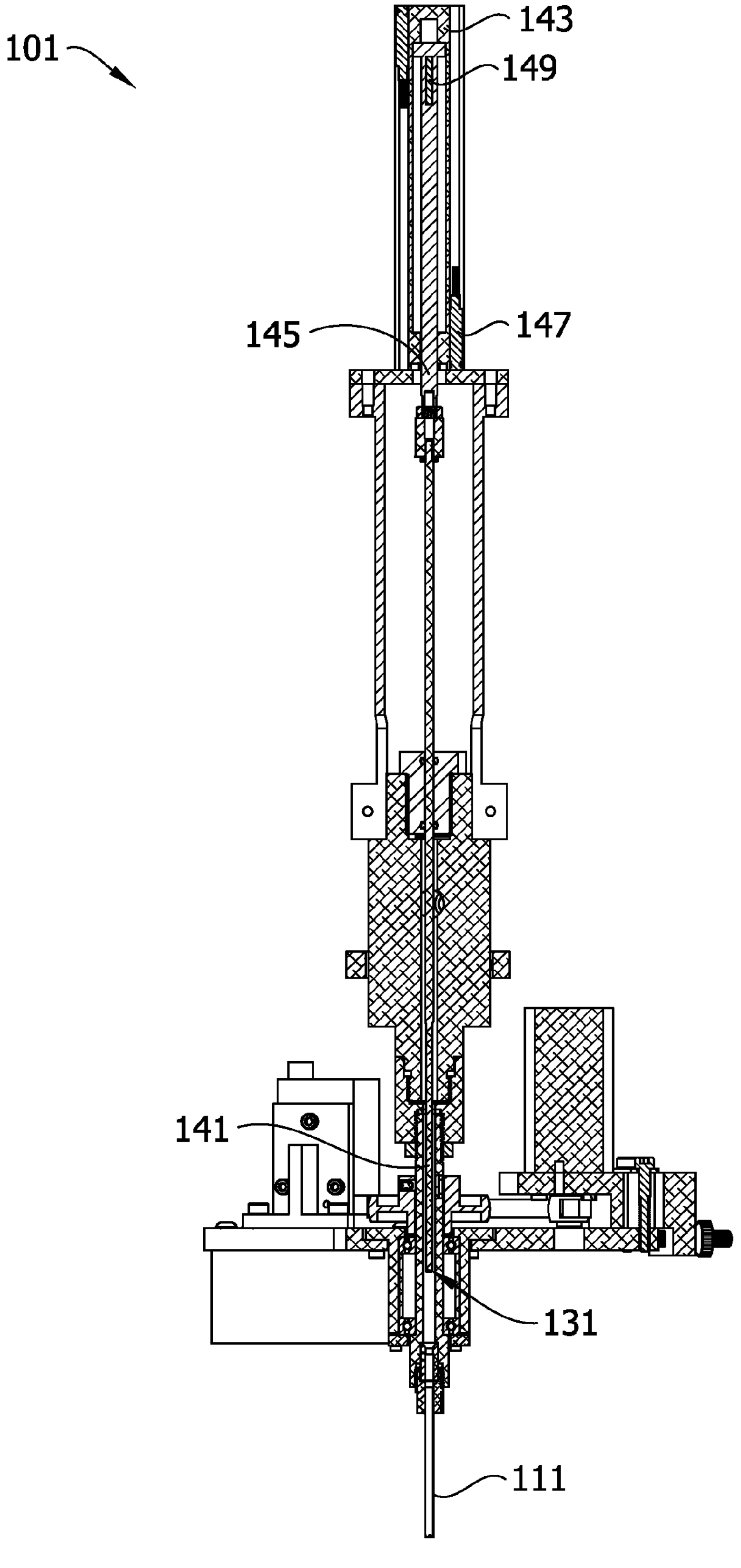
FIG. 5 is a cross section of the robotic end effector taken in a plane including line 5-5 on FIG. 4 and showing an ejector thereof in a retracted position.
Figure 6:
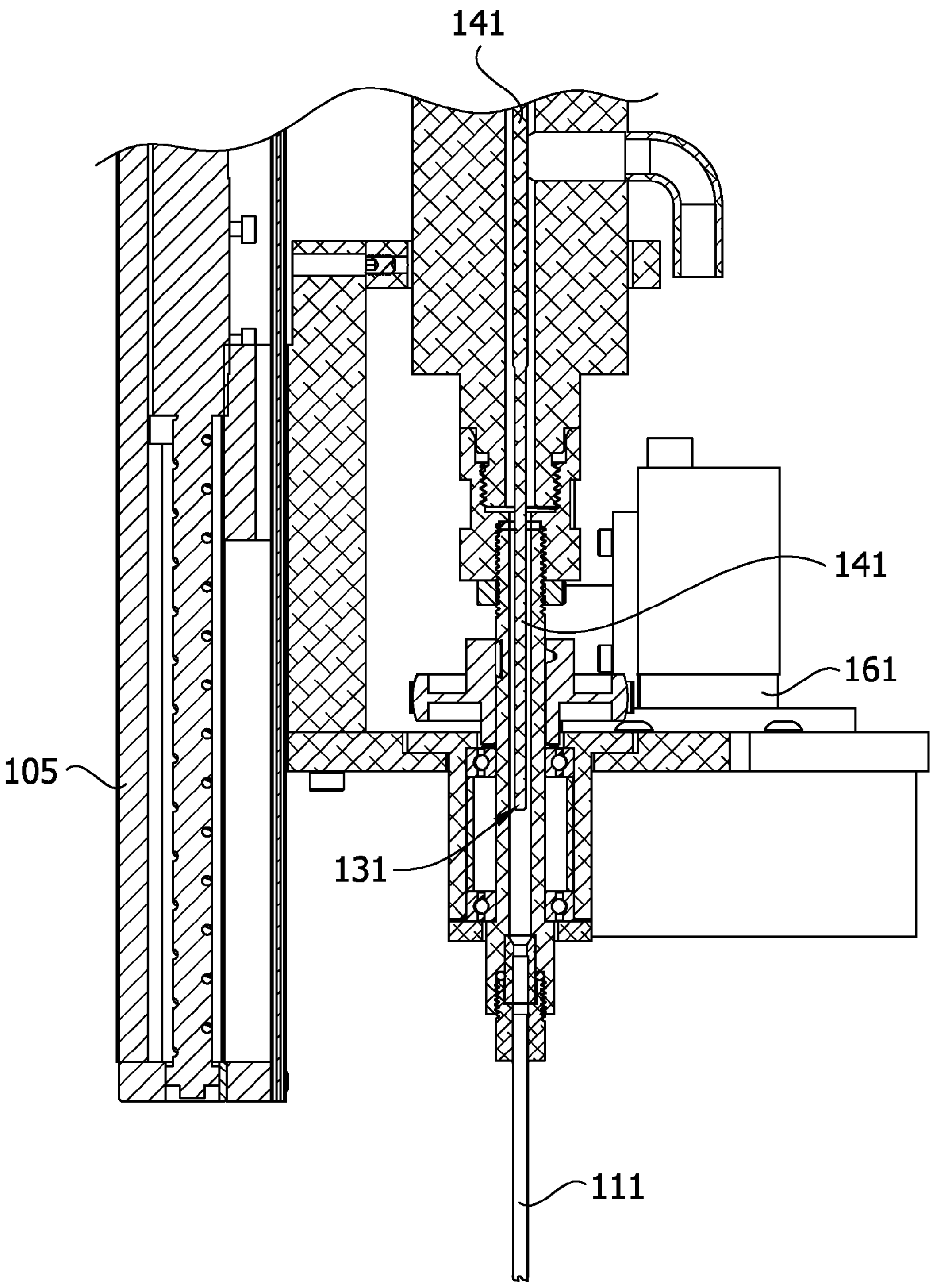
FIG. 6 is an enlarged fragmentary cross section taken in a plane including line 6-6 on FIG. 4 showing the relative positions of the ejector and a coring bit in the retracted position.
Figure 7:
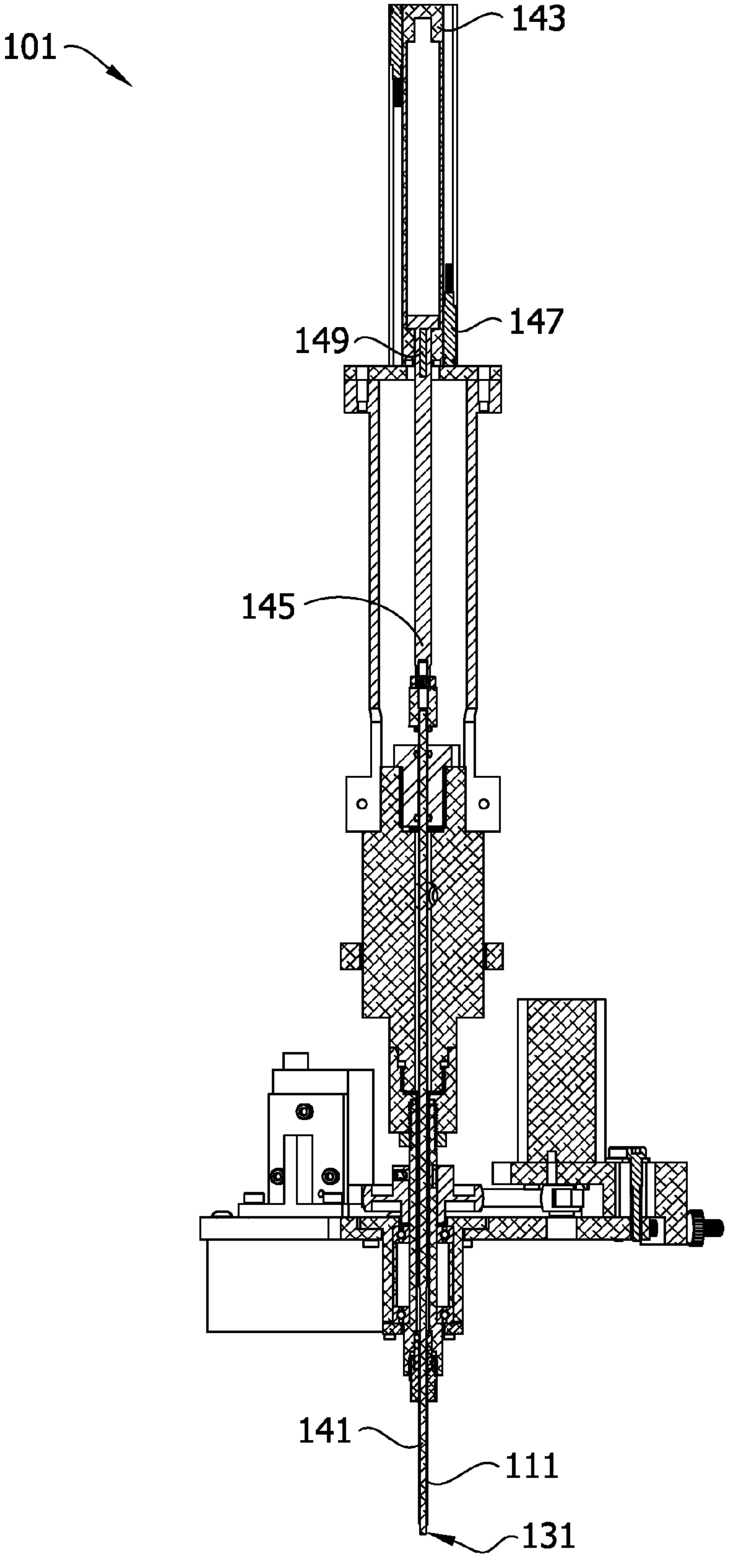
FIG. 7 is a cross section of the robotic end effector similar to FIG. 5 showing the ejector in an extended position.

For example, the end effector 101 suitably includes an ejector 141 adapted to eject a frozen sample core contained in the coring bit 111 from the end of the coring bit. As illustrated in FIGS. 5-8, the ejector 141 is moveable between an extended position in which the ejector extends from a distal end of the coring bit 111 (FIGS. 7 and 8) and a retracted position in which the ejector does not extend from the distal end of the coring bit (FIGS. 5 and 6). The ejector 141 is suitably moveable between the extended and retracted positions by an actuator 143 (e.g., a pneumatic actuator) controlled by the processor. As illustrated in FIGS. 5 and 7, the actuator 143 is mounted at the top of the end effector 101 and the ejector 141 is a plunger operably connected to the rod 145 of the actuator 143 so the ejector moves when the rod of the actuator moves. The end of the ejector 141 that is connected to the rod 145 suitably moves in conjunction with the end of the rod. As the actuator rod 145 moves from its retracted position (FIG. 5) to its extended position (FIG. 7) the end of the ejector opposite the actuator 143 moves through the hollow center of the coring bit 111 all the way past the distal end of the coring bit. Any frozen sample cores retained within the hollow center of the coring bit 111 are thereby ejected out of the end effector 101.

Figure 8:
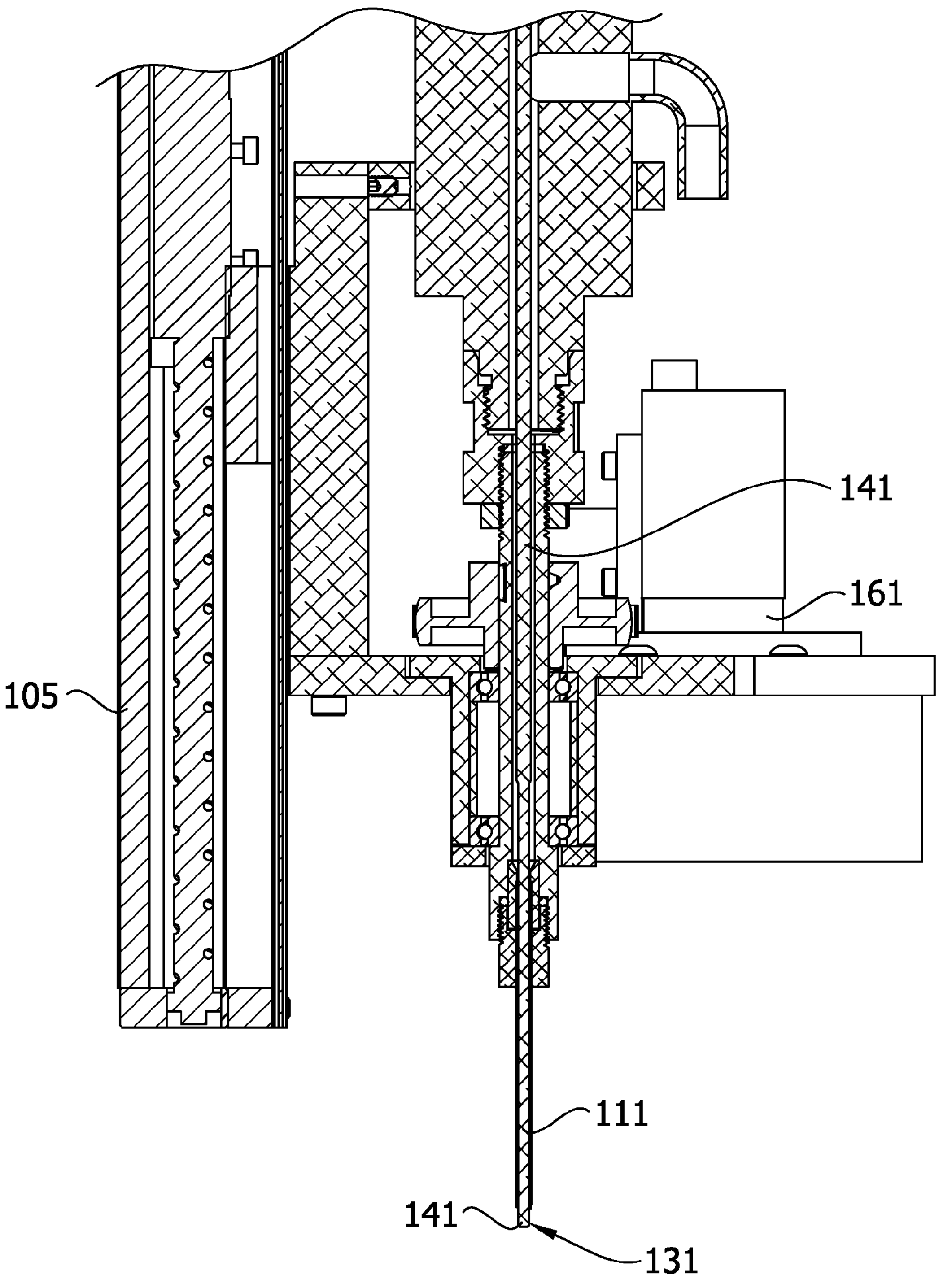
FIG. 8 is an enlarged fragmentary cross section similar to FIG. 6 showing the relative positions of the ejector and coring bit when the ejector is in the extended position.

As illustrated in FIGS. 7 and 8, the ejector 141 is arranged relative to other parts of the end effector 101 so the ejector makes initial contact with a frozen sample when the ejector is in its extended position and the end effector 101 is positioned over a sample and then lowered until it contacts the sample. The fill level detection system 131 includes a sensor 147 adapted to detect contact between the end effector 101 (e.g., the extended ejector 141) and the surface of the frozen sample. Various sensors can be used to detect contact between the end effector 101 and the surface of the frozen sample within the scope of the invention. For one example, the ejector 141 can be adapted to be moved from the extended position toward the retracted position by the frozen sample when the ejector contacts the frozen sample. One way this can be done is by using an actuator 143 that has the capability to be turned off or de-energized once the ejector 141 is in the extended position so the ejector is free to slide back toward the retracted position when the distal end of the ejector contacts the frozen sample. The sensor 147 is suitably a solid state switch or other device that is activated by movement of the ejector from the extended position toward the retracted position. As illustrated for example, the actuator rod 145 includes a magnet 149 or other material that causes a proximity sensor 147 positioned on the actuator adjacent the actuator rod to generate a signal when the magnet or other material moves relative to and the sensor. Suitable pneumatic actuators already having built in sensors to detect movement of the actuator rod can be purchased from SMC Corporation of America or other commercial suppliers.

Another option is to use a sensor that is adapted to detect a change in an electrical property associated with contact between the end effector 101 (e.g., the extended ejector 141) and the frozen sample. Contact between the ejector 141 or other parts of the end effector 101 and the sample can result in various changes, such as a change in impedance, conductivity, capacitance, etc. One or more sensors can be incorporated into the end effector 101 to detect one or more of the electrical changes. Sensors that monitor electrical properties can be used in lieu of the motion activated sensor 147 or in combination with the motion activated sensor.

The fill level detection system 131 can also include an imaging system. For example, the end effector 101 illustrated in the drawings includes a camera 161. The camera 161 is suitably operable to inspect the frozen samples to determine if any frozen sample cores have already been taken from the frozen sample and, if so, to determine the position of a suitable location from which another frozen sample core may be taken from the frozen parent sample. Additional details concerning the use of a camera to inspect frozen samples is provided in U.S. Provisional Patent Application Ser. No. 61/418,688, the contents of which are hereby incorporated by reference. The camera 161 suitably has or can be adjusted to have a narrow depth of field, so only objects within a narrow specified range of distances from the camera are in focus. The processor can be adapted to move the imaging system 161 relative to the surface of a frozen sample (e.g., by moving the entire end effector 101), determine when the imaging system is focused on the surface, and determine the position of the surface of said frozen sample using information about the position of the imaging system when it is focused on the surface of the frozen sample.

As illustrated in FIGS. 11-14B, the fill level detection system 131 can include an end effector 301 having gripper assembly 303 adapted to lift one of the sample containers and a sensor 305 adapted to detect a weight of the lifted container by measuring a force exerted by the lifted container on the end effector. The gripper assembly 303 and weight sensor 305 of the embodiment illustrated in FIGS. 11-14B can be considered one part of a two-part end effector with the other part of the two-part end effector suitably being the end effector 101 described above. Each part 101, 301 of this two-part end effector is suitably in signaling communication with a common processor and positionable relative to the sample containers by the processor and positioning system, although the two parts 101, 301 are not necessarily mounted on the positioning system in the same location and do not necessarily need to be positionable by the positioning system so the two part 101, 301 of the end effector addresses a container simultaneously. For example, the parts 101, 301 of the two-part end effector can suitably be mounted on opposite sides of the cross-beam of a gantry style positioning system. Alternatively, the gripper and weight sensor may be integrated into a single, one-part end effector having the features of the end effector 101 described above within the broad scope of the invention. Further, the fill level detection system 131 does not necessarily need to include any of the features described in connection with the end effector 101 above and may consist entirely of a weight sensing end effector, such as the weight sensing end effector 301, within the broad scope of the invention.

Figure 11:
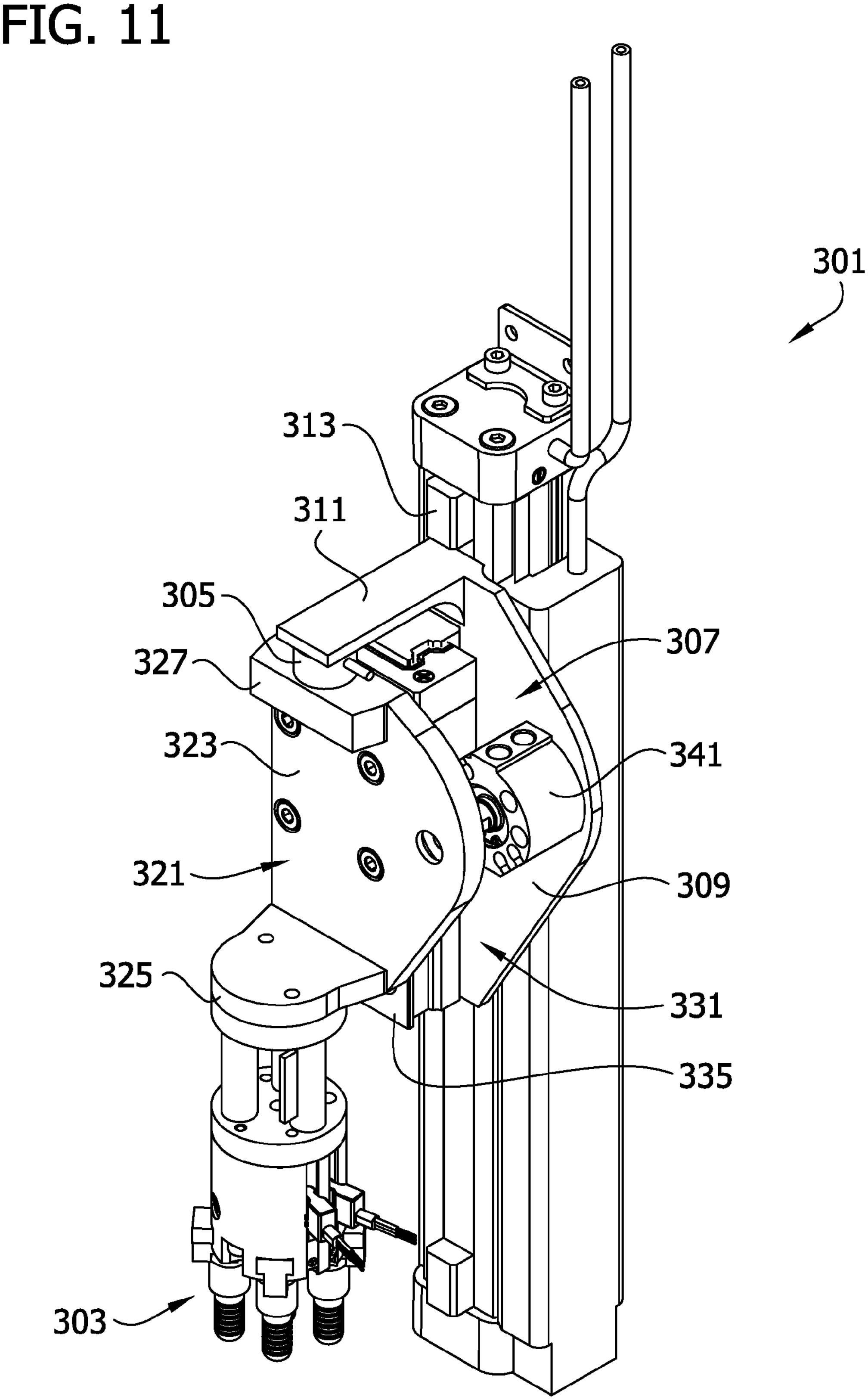
FIG. 11 is a perspective of another embodiment of an end effector of the present invention.
Figure 12:
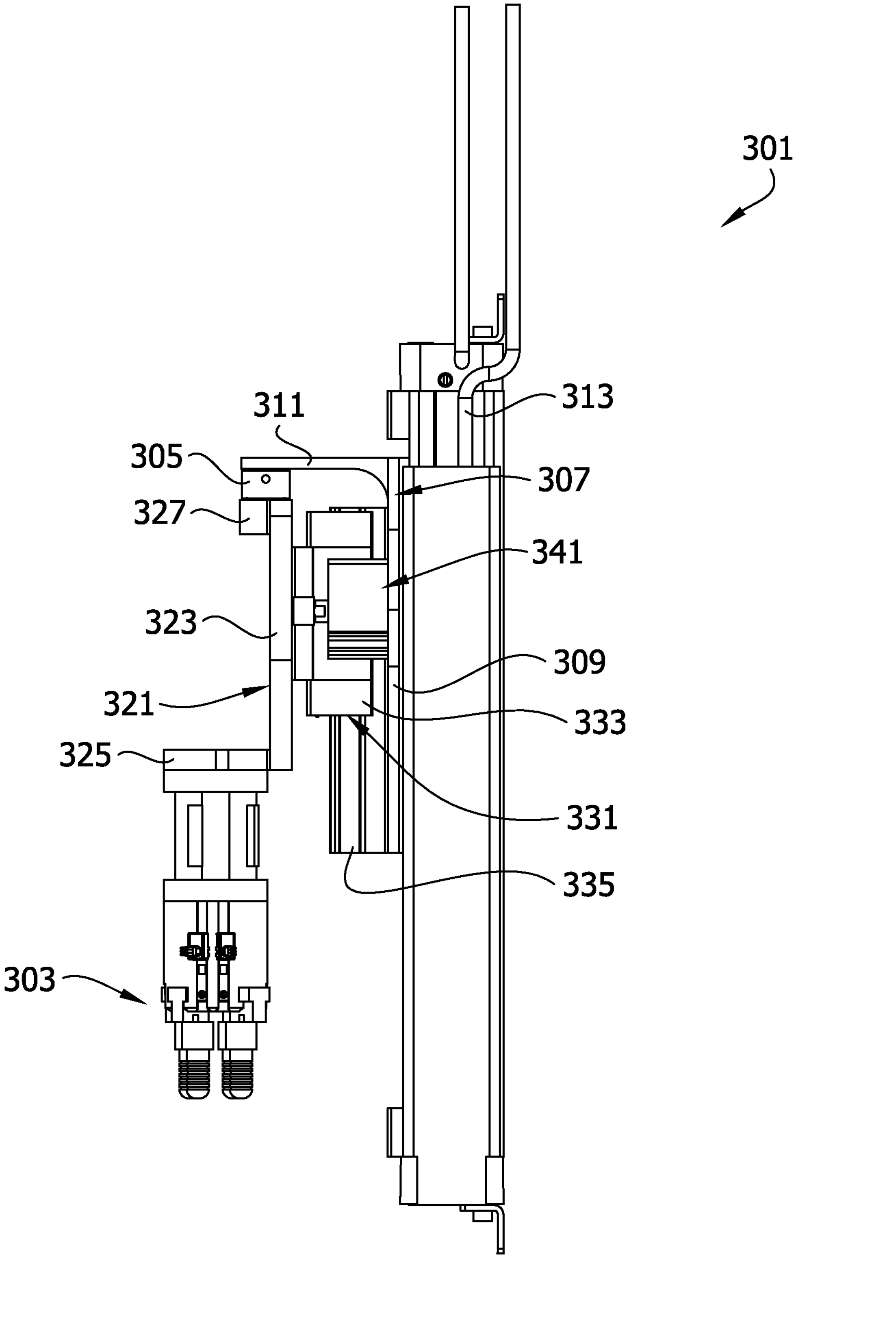
FIG. 12 is a side elevation of the end effector shown in FIG. 11.
Figure 13:
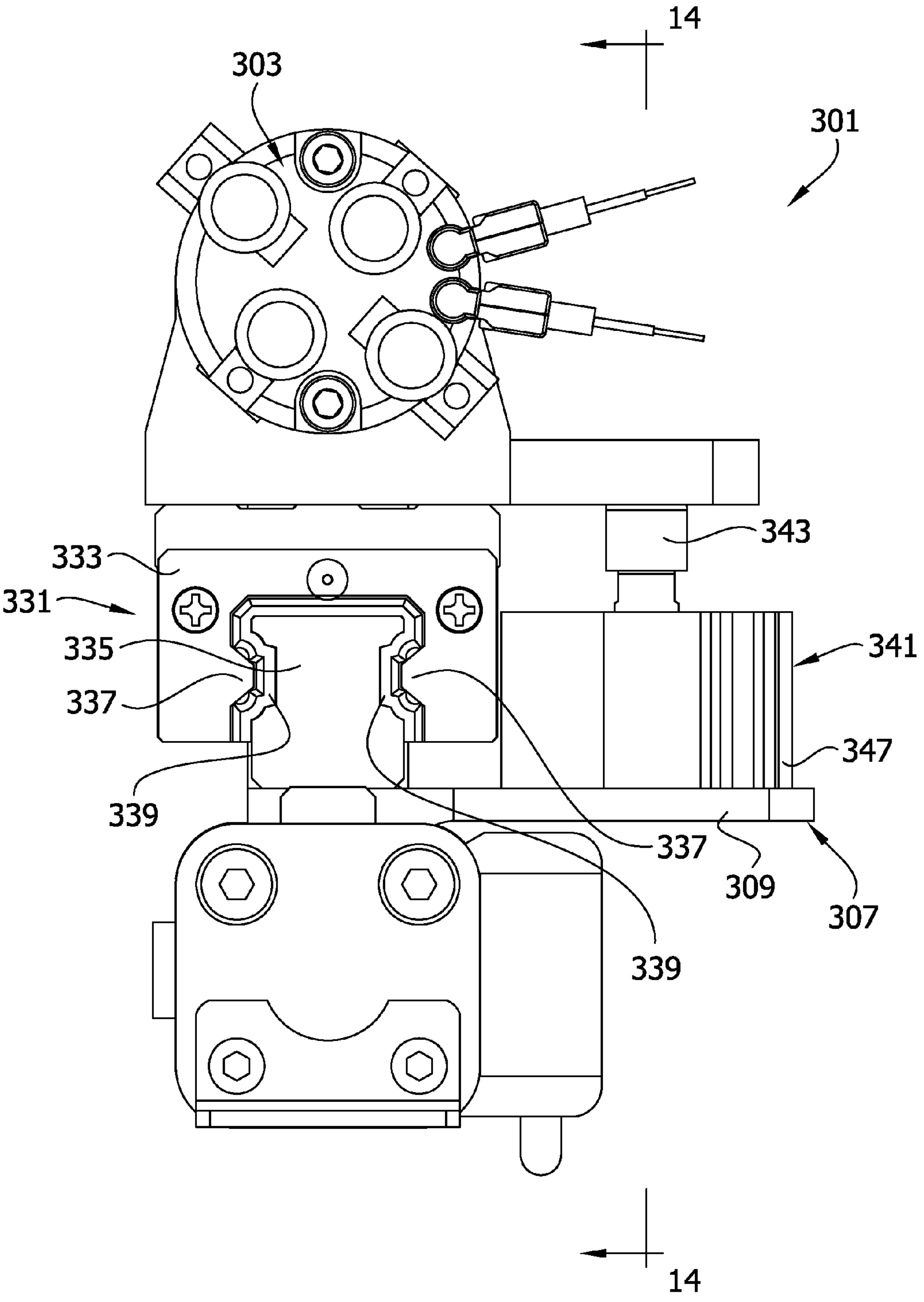
FIG. 13 is a bottom plan of the end effector shown in FIG. 11.

Referring to FIGS. 11-13, the end effector 301 includes a frame 307. The size, shape, and configuration of the frame can vary widely within the scope of the invention. As illustrated, the frame 307 includes a plate 309 and an arm 311 extending laterally from the plate. The frame 309 is suitably mounted on or serves as a Z-axis carriage that can be driven back and forth (e.g., vertically) by a z-axis motor or actuator 313.

The gripper assembly 303 is operable to selectively hold and release a container containing sample material. For example, the gripper assembly 303 is suitable for selectively lifting a container off a work platform (not shown), transporting the container to a different location, and then setting the container down and letting go of it. Thus, the gripper assembly 303 allows the effector 301 to operate as a pick and place end effector. Details concerning the construction and operation of robotic gripper assemblies are well known to those skilled in the art and do not need to be set forth herein. The gripper assembly 303 illustrated in the drawings has a plurality of moveable fingers 315 (e.g., four fingers) that are selectively moveable from a hold configuration in which the fingers are positioned to hold a container and a release configuration in which the fingers are positioned to release the container. When the fingers 315 are in the hold configuration, the gripper assembly 303 can hold a container containing a sample material in a suspended position such that the gripper assembly bears the weight of the container and any sample material therein. Suitable gripper assemblies can be purchased from numerous different commercial suppliers. The gripper assembly 303 illustrated in the drawings is just one of many options that can be used within the scope of the invention.

The gripper assembly 303 is mounted on a mounting bracket 321. The size, shape, and configuration of the mounting bracket can vary widely within the broad scope of the invention. As illustrated, the mounting bracket 321 includes a plate 323 and a pair of laterally-extending arms 325, 327 at opposite ends of the plate. The gripper assembly 303 is mounted on the lower arm 325 in the illustrated embodiment. A linear bearing 331 connects the mounting bracket 321 to the frame 307. As illustrated, for example, the linear bearing includes a runner block 333 mounted on a rail 335 for sliding movement of the runner block relative to the rail. As illustrated in FIG. 13, the rail 335 has channels 339 on opposite sides and the runner block 333 has arms 337 that extend into the channels 339. Bearings (not shown) are positioned between the runner block 333 and rail 335 to facilitate sliding movement of the runner block along the rail. The linear bearing 331 limits movement of the runner block 333 in all directions except axially along the rail 335. The plate 323 of the mounting bracket 321 is mounted on the runner block 333 and the rail 335 is mounted on the frame 307. The linear bearing 331 is oriented to allow movement of the mounting bracket 321 relative to the frame 307 in a vertical direction while limiting movement of the mounting bracket relative to the frame in all lateral directions.

The weight sensor 305 connects the frame 307 to the mounting bracket 321. For example, the weight sensor 305 suitably connects the arm 311 of the frame to the upper arm 327 of the mounting bracket. The weight sensor 305 is suitably a highly sensitive strain gauge, load cell or other sensor that is adapted to output a signal indicative of an amount of force transferred between the frame and mounting bracket through the weight sensor. For example, the weight sensor 305 is suitably adapted to detect and measure a force in the range of 0 to about 8 Kg. The weight sensor 305 is also is sufficiently sensitive to accurately measure variations (e.g., as small 0.5 mg, and more desirably as small as 0.1 mg) in the weight of sample containers held in suspension by the gripper assembly 303. The weight sensor 305 is suitably sufficiently accurate to maintain a full scale deviation of 0.3 percent or less.

The end effector 301 includes a locking system 341 that is selectively configurable between a first configuration in which the locking system limits movement of the mounting bracket 321 relative to the frame 307 and bears at least some of the weight of the mounting bracket and a second configuration in which the locking system does not bear any of the weight of the mounting bracket and the weight sensor bears substantially the entire weight of the mounting bracket (including the weight of the gripper assembly 303 and anything held in suspension by the gripper assembly). For example, the locking system 341 in the illustrated embodiment includes a pin 343 that is selectively moveable between a locking position and a non-locking position. When the pin 343 is in the locking position (FIG. 14A), the pin is received in an opening 345 in the mounting bracket 321 so the pin blocks movement of the mounting bracket relative to the frame. When the pin 343 is in the non-locking position (FIG. 14B), the pin is at least partially withdrawn from the opening 345 and does not block movement of the mounting bracket 321 relative to the frame 307. In the illustrated embodiment, the locking system 341 includes an actuator 347 (e.g., a pnematic actuator, solenoid, or other electronically controllable actuator) that is mounted on the plate 309 of the frame 307 and adapted to move the pin 343 between the locking and non-locking positions. The side of the opening 345 facing the pin 343 is suitably funnel-shaped to facilitate movement of the locking pin to the locking position even if the pin is not precisely aligned with the opening when the pin begins movement into the opening. Likewise, the head of the pin 343 has rounded or beveled shoulders to further facilitate insertion of the pin in the opening 345 even if there is slight misalignment between them when the insertion begins.

In some cases, the weight sensor 305 can be part of or constitute the fill level detection system. For example, when the tare weight of the containers and features of the frozen samples contained therein (e.g., density of the sample material, number of frozen sample cores already taken from the frozen samples, container configuration, etc.) are already characterized or can be characterized by the processor, the weight of the sample-filled container provides an indication of the level to which the container is filled with sample material. In other cases, the processor can use information from the weight sensor 305 to provide additional verification that a frozen aliquot contains at least a minimum required amount of frozen sample without necessarily being used by the processor to determine the fill level of the container, as will be outlined in more detail in the methods described below.

Figure 9A:
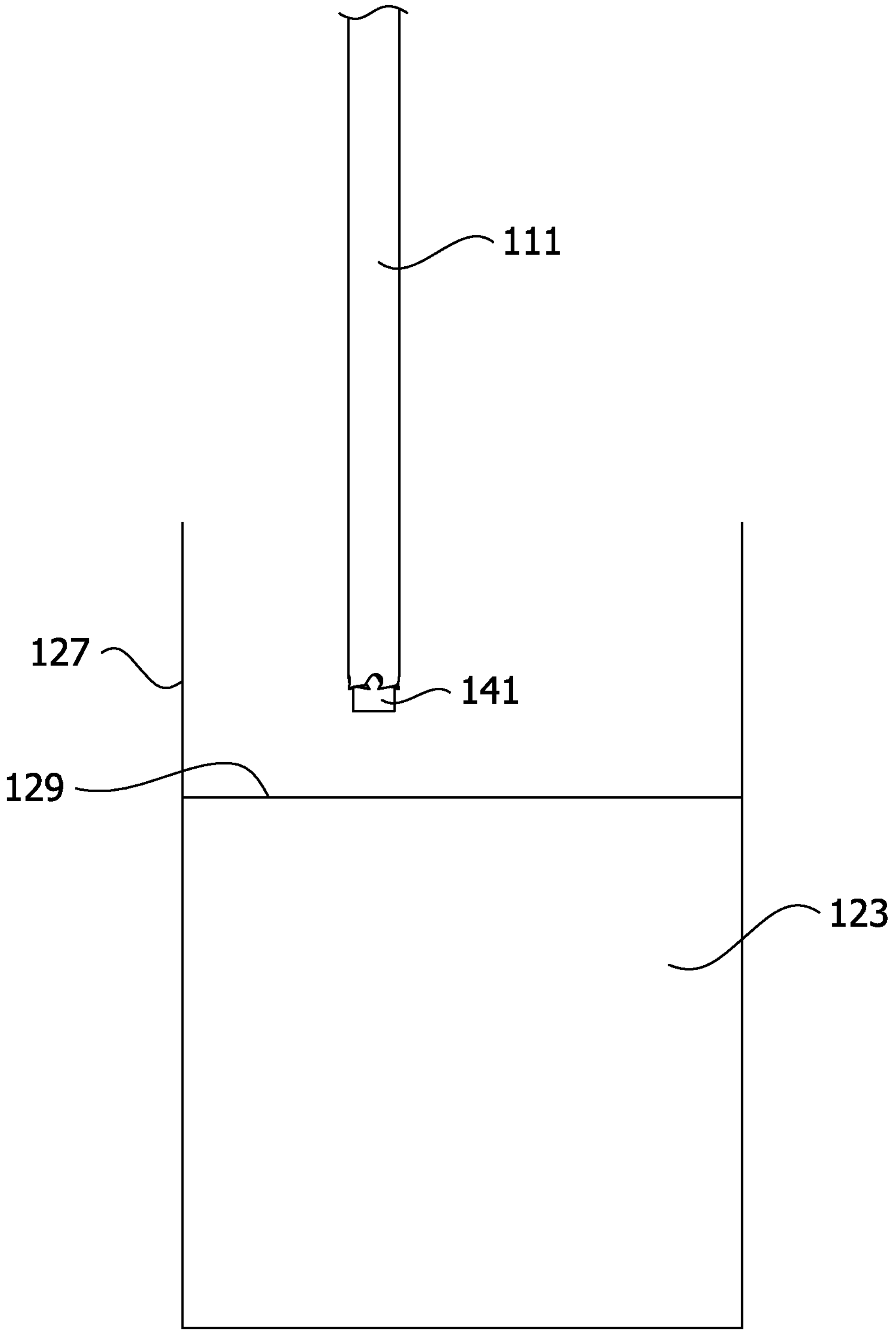
FIGS. 9A-9H illustrate one embodiment of a method of using the end effector to take frozen sample cores from a frozen sample.
Figure 9B:
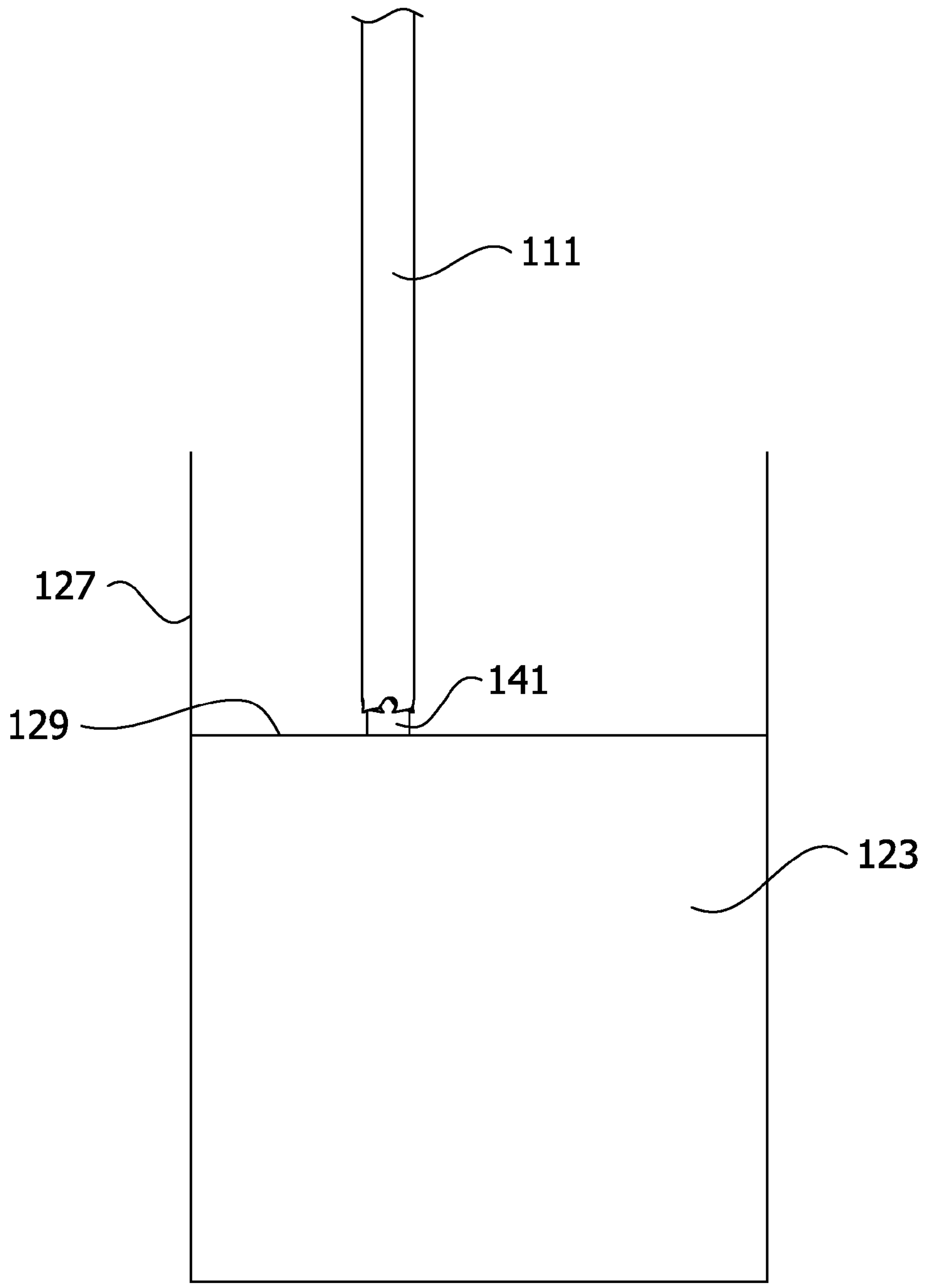

FIGS. 9A-9H illustrate one embodiment of a method of using the end effector 101 to obtain a frozen aliquot that has a predetermined minimum amount of sample material. First, the sensor 147 is used to find the position of a surface 129 of the frozen sample 123 that is spaced from a bottom of the container 127 and output a signal indicative of the position of the surface to the processor. The actuator 143 moves the ejector 141 to the extended position and the positioning system positions the coring bit 111 into alignment with the frozen sample (e.g., above the sample as illustrated in FIG. 9A). Then the Z-axis motor 103 moves (e.g., lowers) the end effector 101 until the extended ejector 141 contacts the surface of the frozen sample, as illustrated in FIG. 9B. At this point, the frozen sample 123 pushes the ejector 141 back into the coring bit 111 toward the retracted position as the Z-axis motor 103 continues to move the coring bit closer to the sample surface 129. This relative movement between the ejector 141 and the coring bit 111 causes the magnet 149 on the actuator rod 145 to move relative to the sensor 147. The sensor 147 detects this movement and sends a signal to the processor indicating the ejector 141 has contacted the frozen sample surface. The processor uses the information about the position of the ejector 141 and/or coring bit 111 (e.g., from the positioning system and/or Z-axis motor) to determine the position of the sample surface.

Figure 9C:
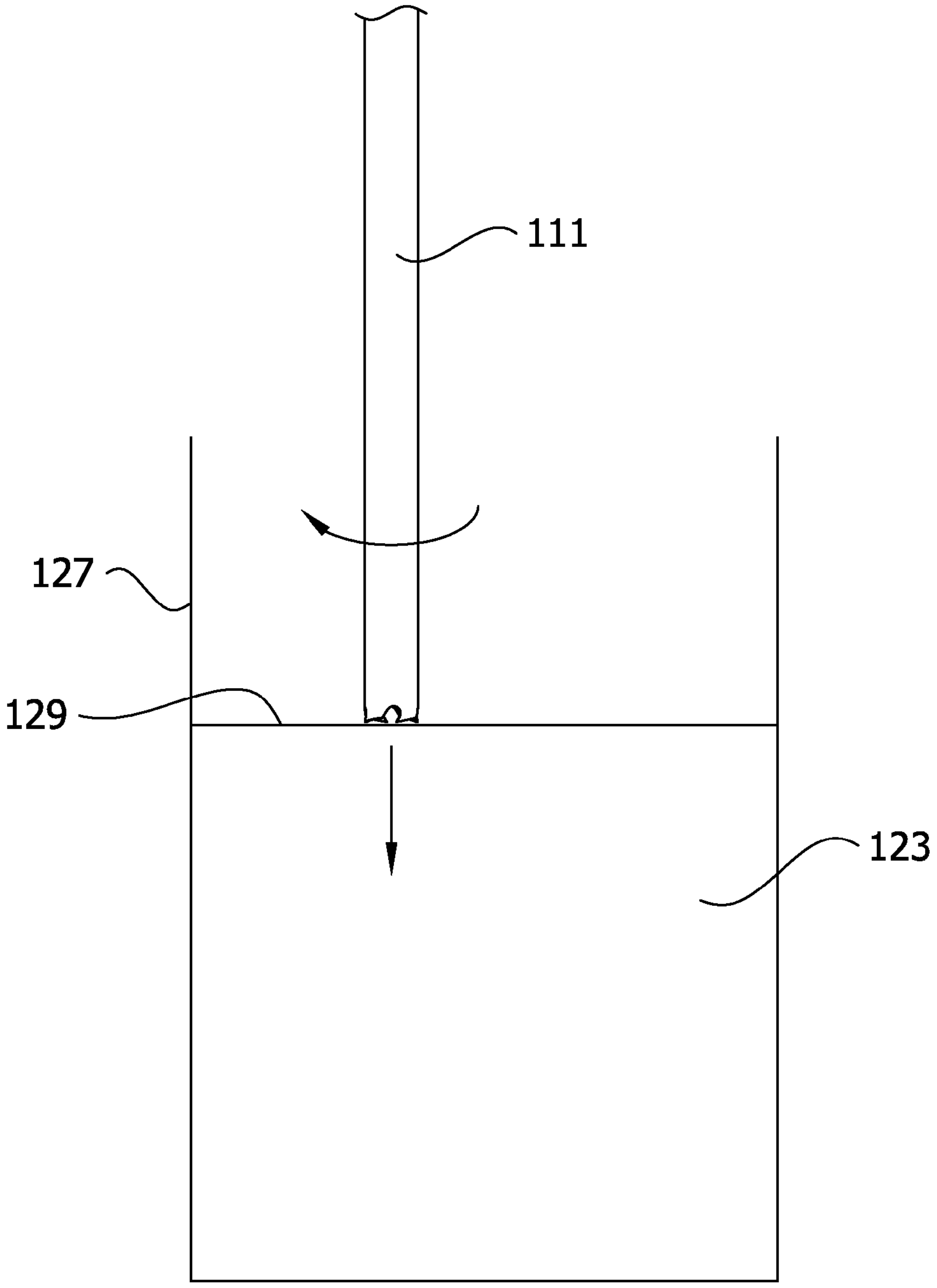
Figure 9D:
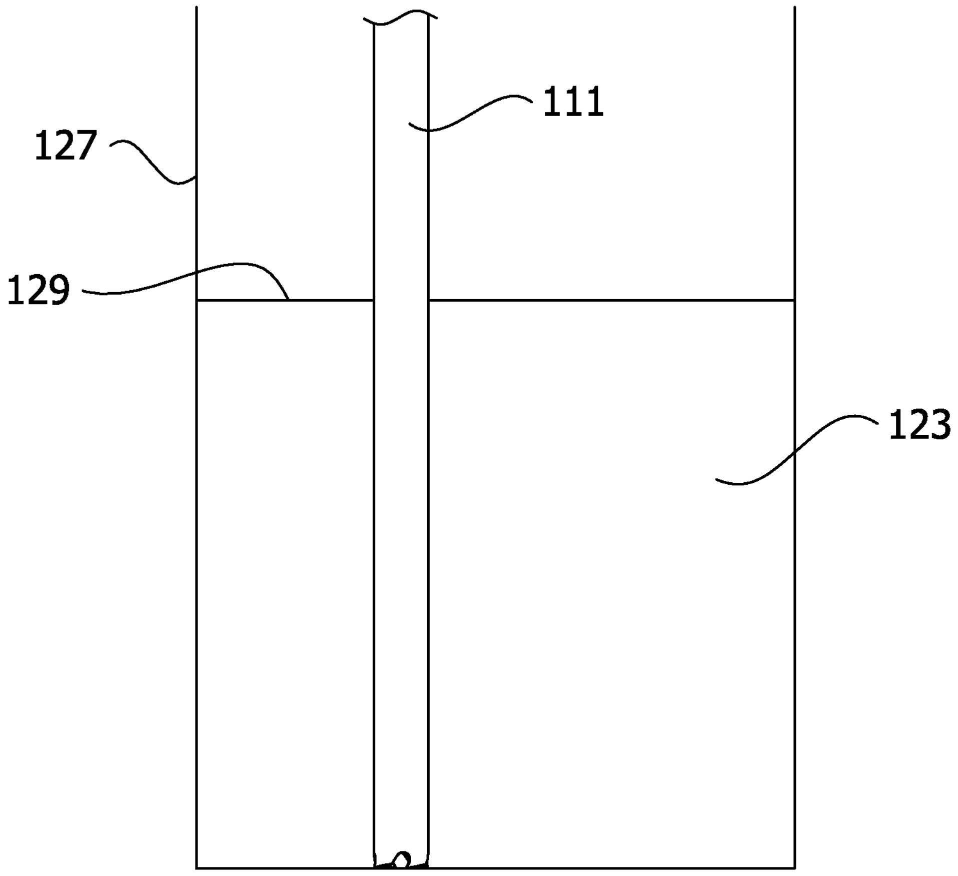

The ejector 141 is moved to its retracted position by the actuator 143. The motor 115 rotates the coring bit 111 while the Z-axis motor 103 robotically inserts the tip of the coring bit into the frozen sample 123 under the guidance of the processor to a position within the frozen sample, as illustrated in FIGS. 9C and 9D. The position of the frozen sample surface 129 corresponds to the length of the frozen sample core 125 that can be obtained by extending the coring bit a particular distance into the frozen sample, e.g., all the way through the sample to the closed end (e.g., bottom) of the container as depicted in FIG. 9D. It is often desirable to extend the coring bit 111 all the way through the frozen sample 123 to obtain a full-depth frozen sample core because vertical concentration gradients can develop as the sample is being frozen and the overall composition of full-depth frozen sample cores can therefore be more representative of the overall composition of the entire parent sample. Even if the coring bit 111 is not extended all the way through the frozen sample 123 to obtain a full-depth frozen sample core 125, the processor can use the information about the position of the sample surface 129 to determine how much material is in a frozen sample core obtained by moving the coring bit 111 a particular distance into the frozen sample 123.

Figure 9E:
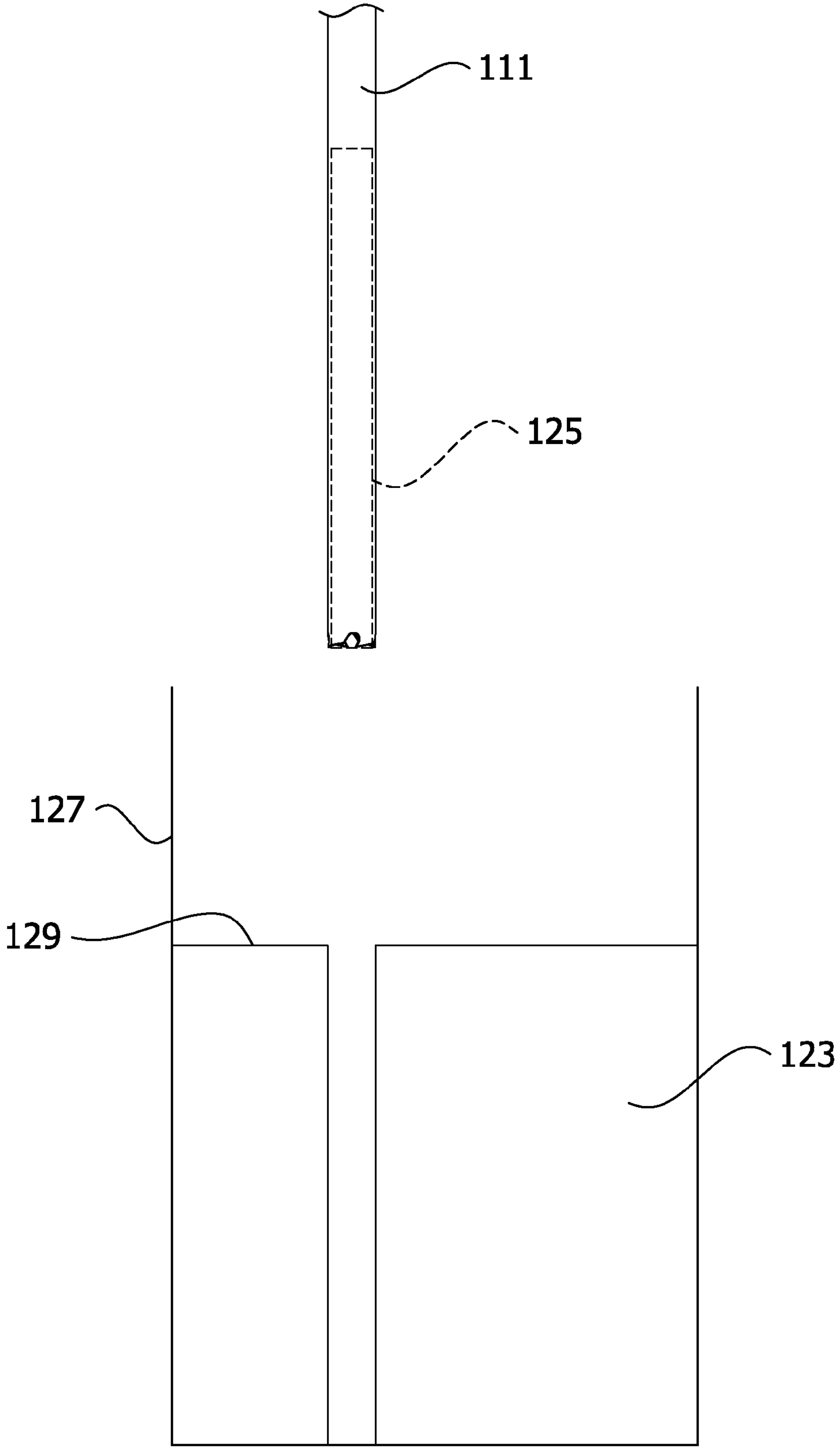
Figure 9F:
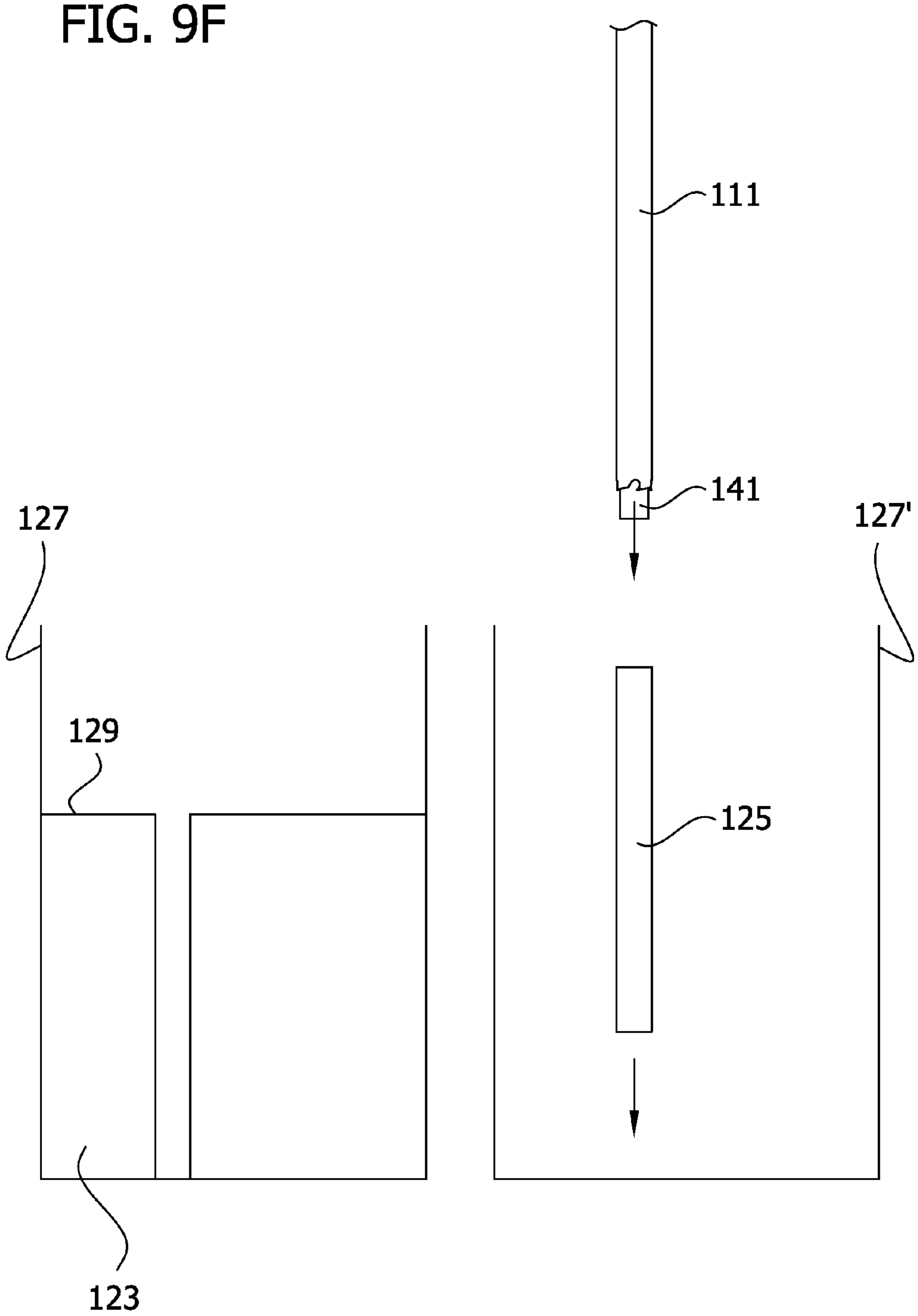
Figure 9G:
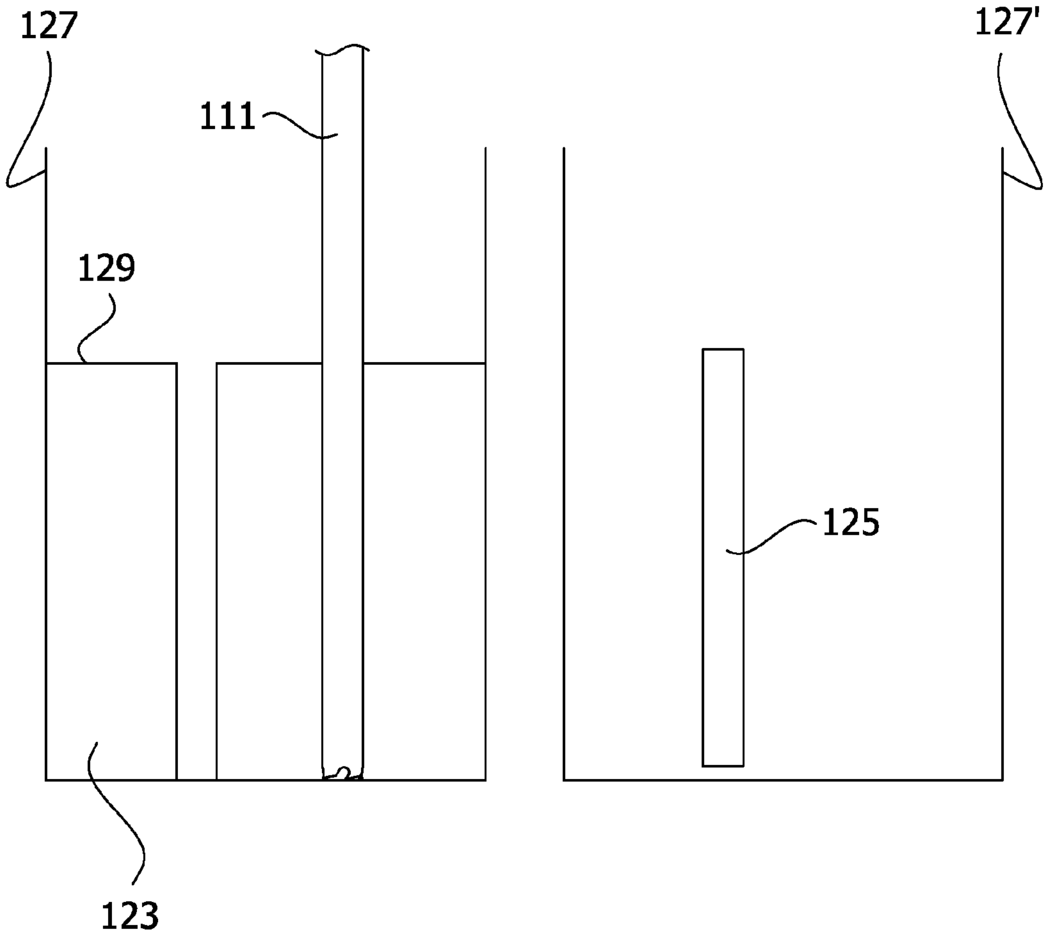
Figure 9H:
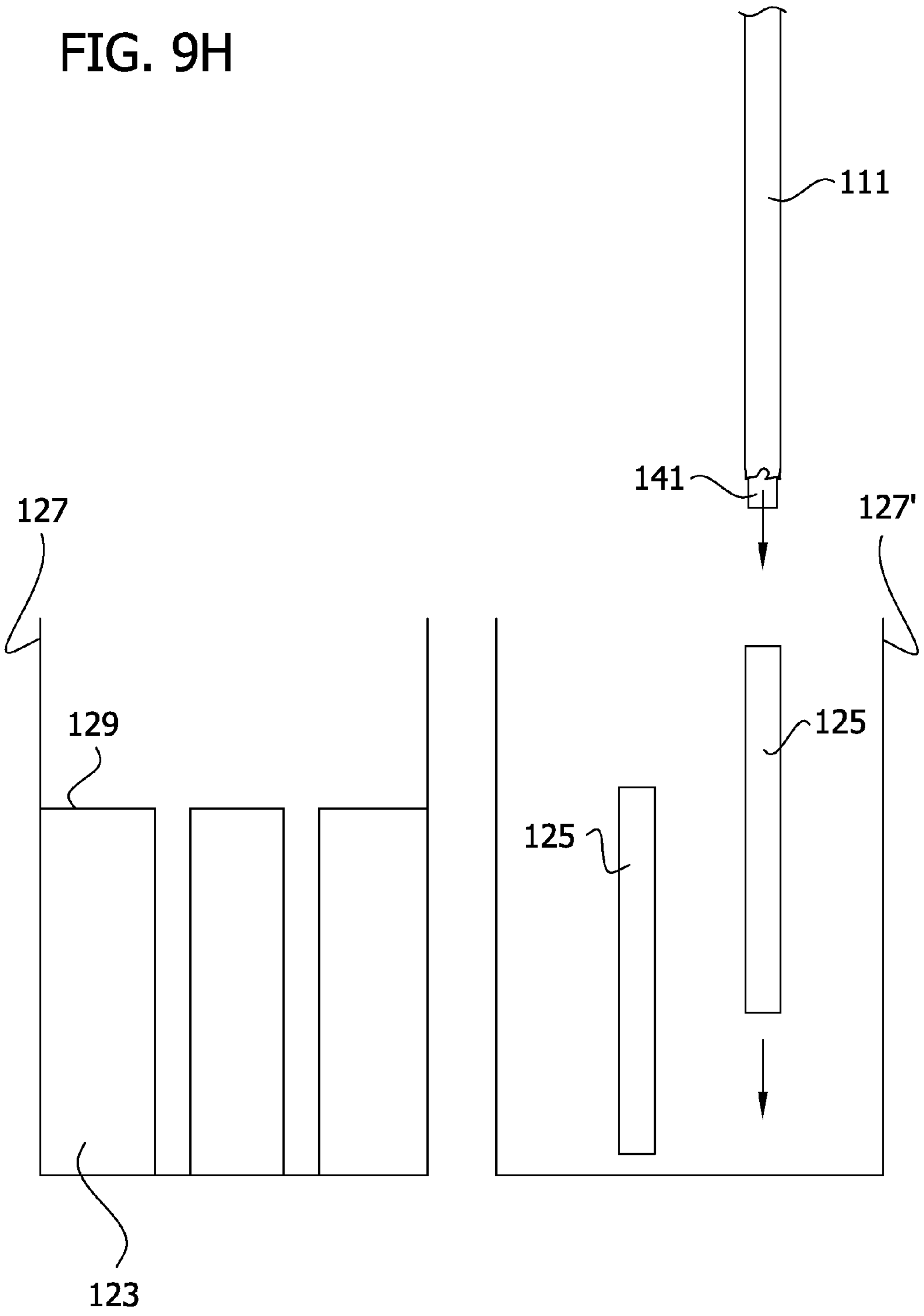
Figure 10A:
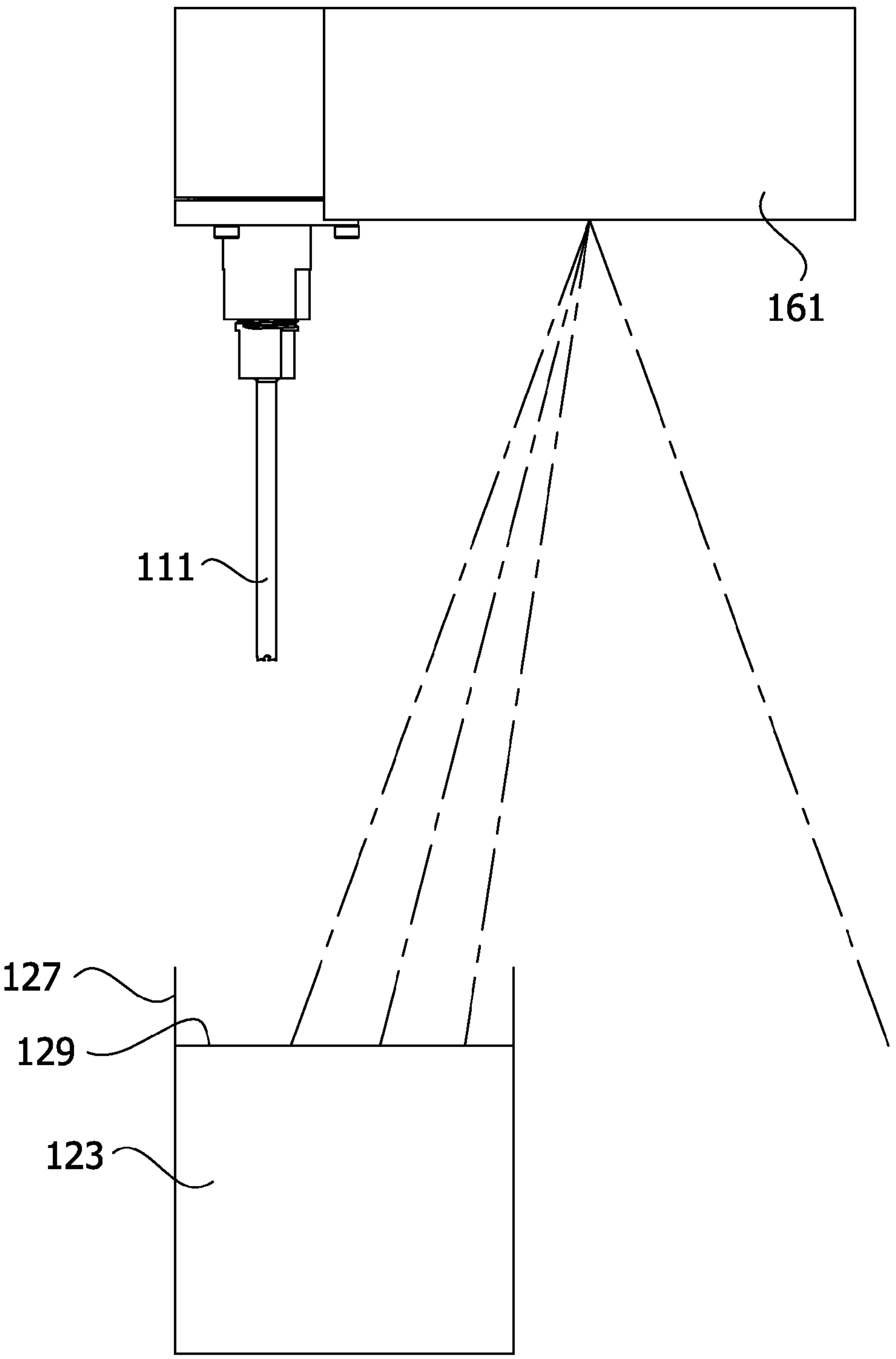
FIGS. 10A-10D illustrate another embodiment of a method of using the end effector to take frozen sample cores from a frozen sample.
Figure 10B:
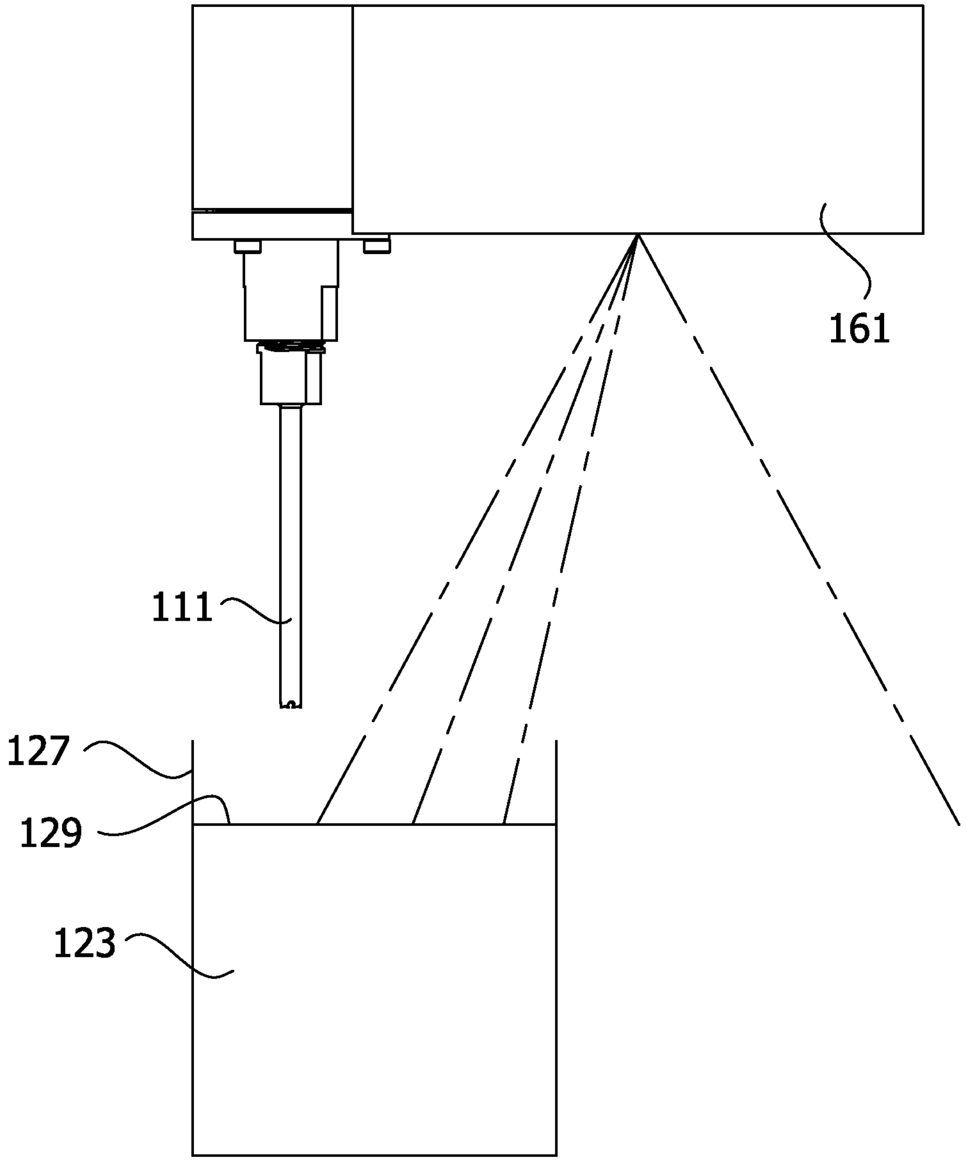
Figure 10C:
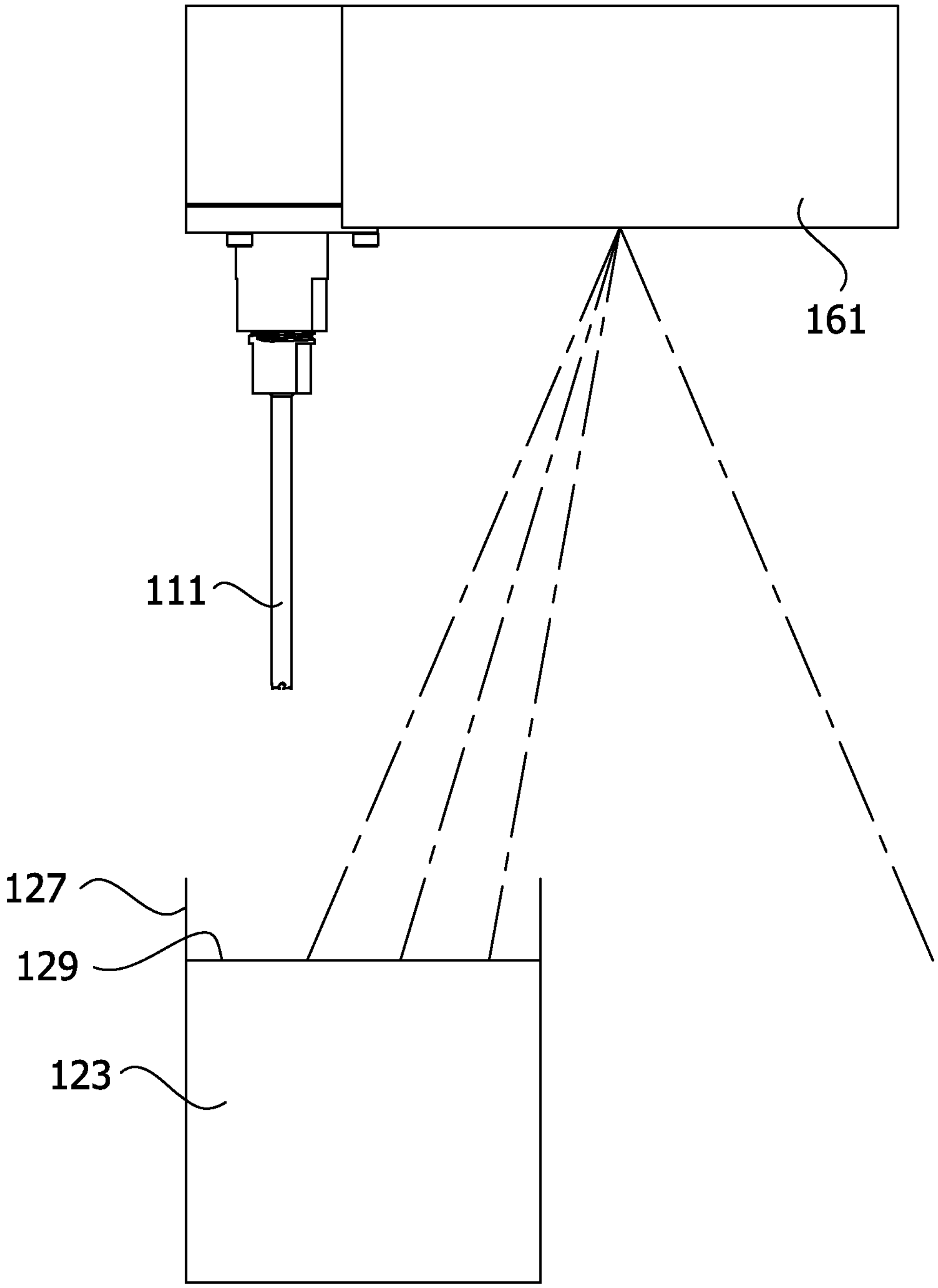
Figure 10D:
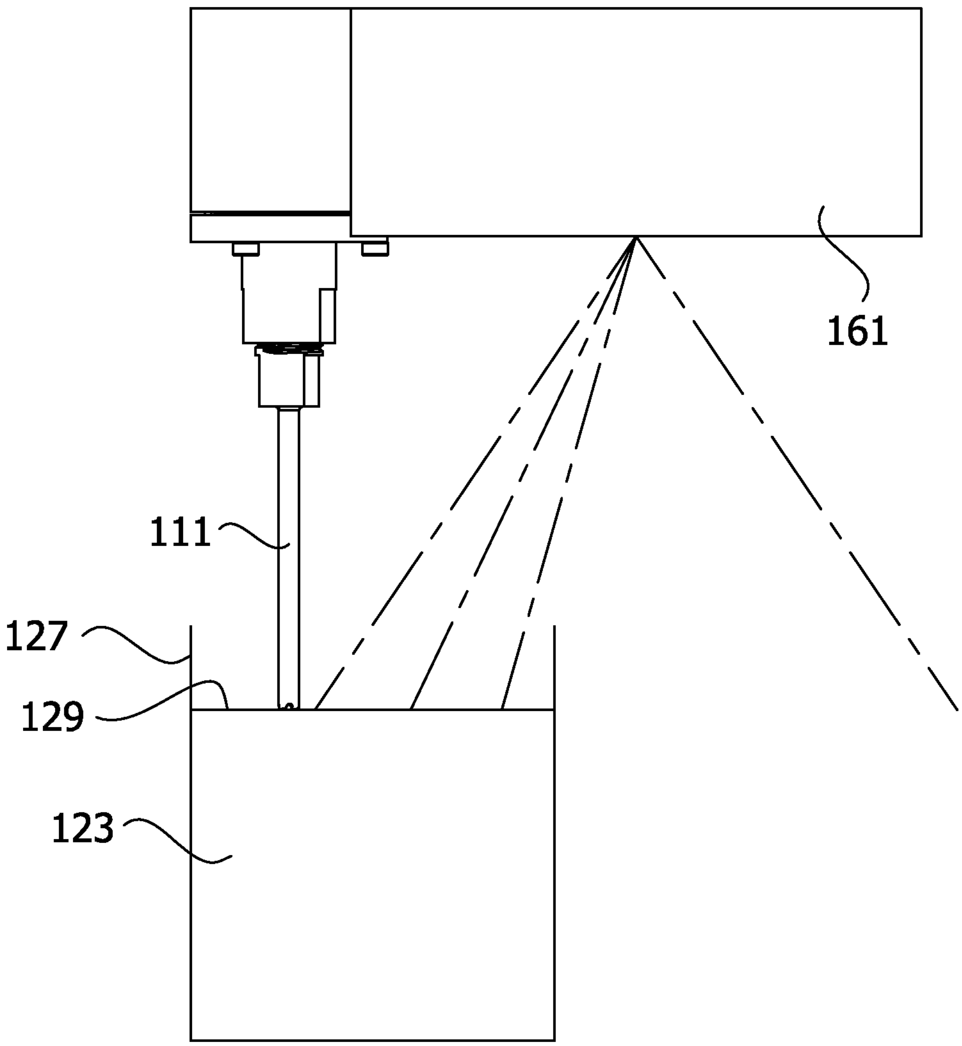

After drilling is complete, the Z-axis motor 103 robotically withdraws the coring bit 111 from the frozen sample 123 to obtain a frozen sample core 125 that will form at least part of the frozen aliquot. The frozen sample core 125 is retained within the coring bit 111 after the coring bit is withdrawn from the sample 123 as illustrated in FIG. 9E. The positioning system moves the coring bit 111 to a frozen aliquot receiving container 127' and the ejector 141 ejects the frozen sample core into the aliquot receiving container, as illustrated in FIG. 9F.

The processor uses information about the position of the surface 129 of the frozen sample 123 the depth to which the coring bit 111 is inserted in the frozen sample to determine whether or not the frozen sample core 125 contains at least the predetermined minimum volume of sample material. If the first frozen sample core 125 contains enough material, the process ends at FIG. 9F when the frozen sample core is deposited in the aliquot receiving container 127'. However, if the initial frozen sample 125 core does not contain enough material, the process is repeated (FIGS. 9G-9H) and the coring bit 111 is used to obtain another frozen sample core 125 and deposit it in the aliquot receiving container 127' until the frozen aliquot contains at least the minimum amount of material needed for the test. In the illustrated embodiment, each frozen sample core 125 that is obtained and deposited in the aliquot receiving container 127' is a full-depth core, which can help ensure the overall composition of the aliquot is more representative of the composition of the entire parent sample 123. However, if the frozen sample 123 does not contain vertical concentration gradients and/or it is not important for the composition of the aliquot to match the overall composition of the sample, the processor can interrupt the process of drilling a frozen sample core before the coring bit 111 reaches the opposite end of the sample within the scope of the invention. After a sufficient number of frozen sample cores 125 have been deposited in the aliquot receiving container 127' to form an aliquot containing at least the minimum amount of sample material, the container 127 containing the remaining frozen parent sample material 123 is suitably returned to a cryopreservation unit and stored for further use at a later time.

Another embodiment of a method of using the robotic end effector 101 is illustrated in FIGS. 10A-10D. In this embodiment, the processor uses the imaging system 161 to identify the position of the frozen sample surface 129. Once the positioning system has aligned the coring bit 111 with the frozen sample 123 (FIG. 10A), the Z-axis motor 103 moves the camera 161 toward and/or away from the frozen sample (e.g., as in FIGS. 10A-10C) until the frozen sample surface 129 is in focus. The processor recognizes when the sample surface 129 is in focus (e.g., using well-known autofocus technology) and uses information about the position of the imaging system 161 when the sample surface is in focus to determine the position of the sample surface 129. Once the processor has determined the position of the frozen sample surface 129, one or more frozen sample cores 125 are obtained from the frozen sample 123 and deposited in the aliquot receiving container 127' in substantially the same manner described above in connection with FIGS. 9C-9H.

Figure 14A:
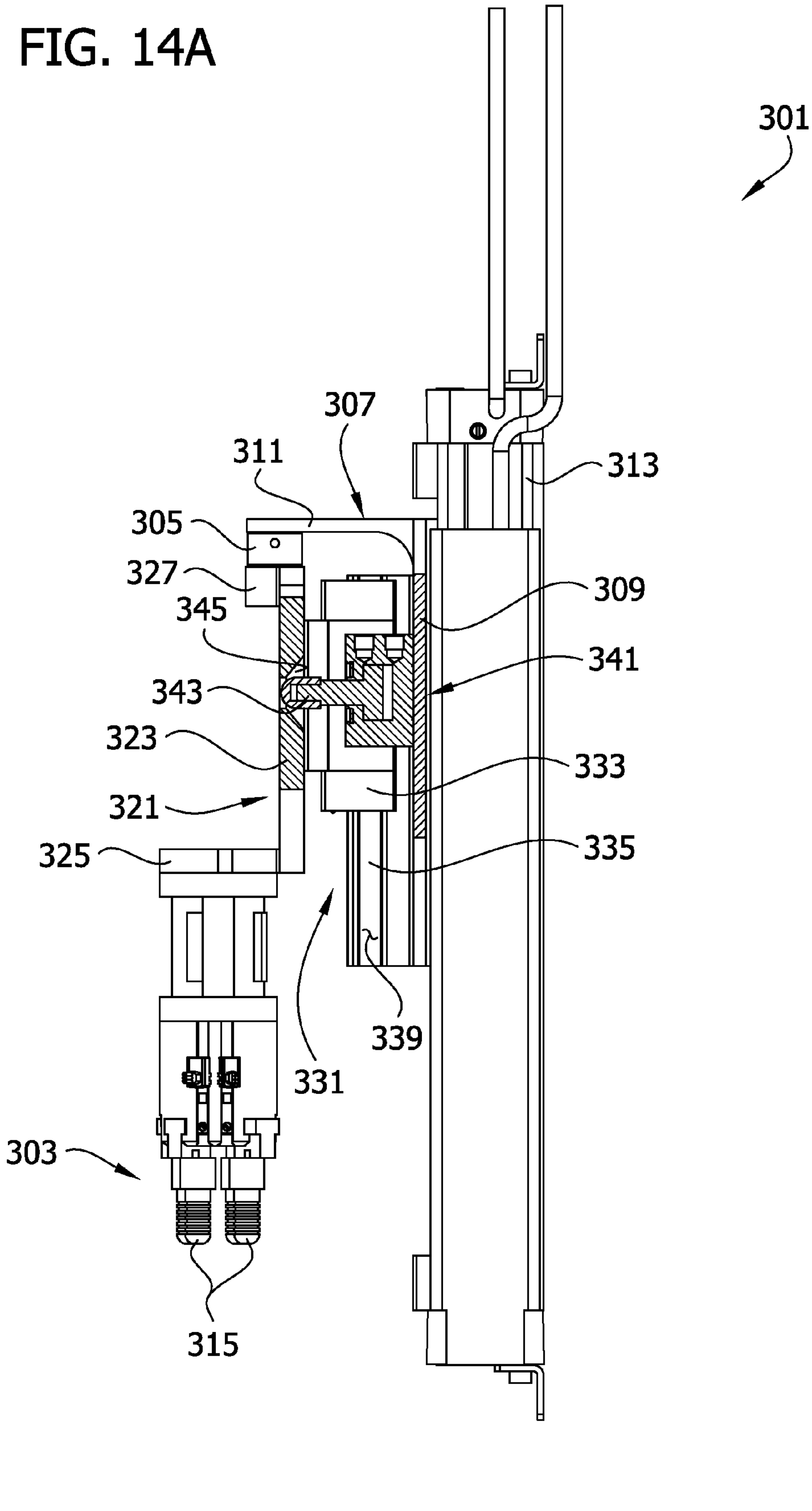
FIGS. 14A and 14B are cross sections of the end effector shown in FIG. 11 taken in a plane including line 14-14 on FIG. 13, FIG. 14A illustrating the end effector in a configuration to transporting a container and FIG. 14B illustrating the end effector in a configuration for weighing a container.
Figure 14B:
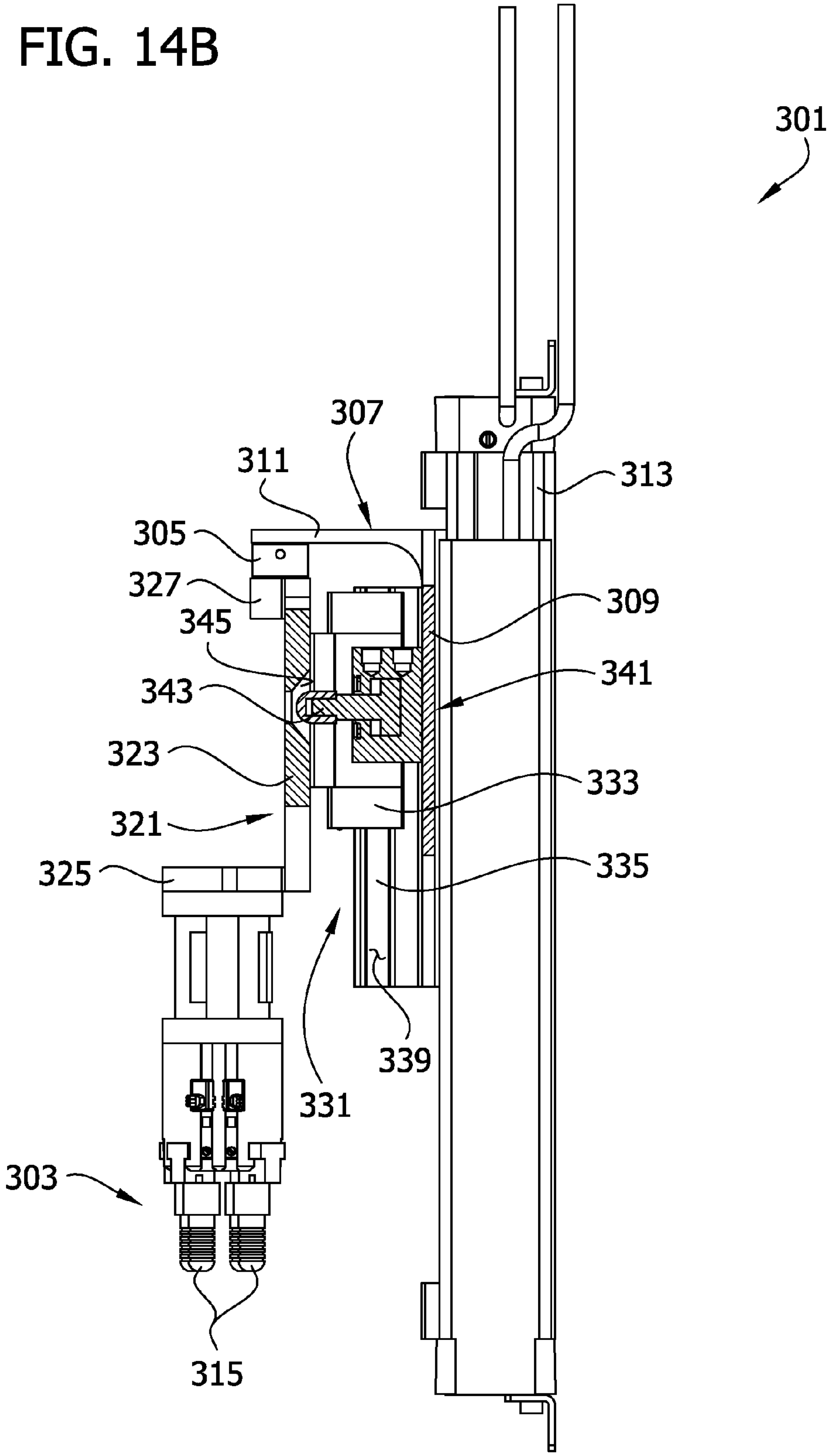

In one method of using the end effector 301 to weigh a container and/or determine the fill level of a container, the locking pin 343 is first inserted into the opening 345 to block movement of the mounting bracket 321 relative to the frame, as illustrated in FIG. 14A. Then the gripper assembly 303 is used to pick up a container (e.g., a container containing a frozen sample material). For example, the gripper assembly 303 can be used to pick up one sample container from an array of sample containers in preparation of moving the container to a station on a work platform where one or more frozen sample cores will be taken from the container (e.g., using the other part 101 of the end effector, as illustrated in FIGS. 9A-9H). The locking pin 343 is suitably kept in the locking position while the end effector 301 lifts and moves the container. This advantageously shields the sensitive weight sensor 305 from experiencing the loads associated with accelerations of the container, gripper assembly 303, and mounting bracket 321. The loads associated with these accelerations are transmitted to the frame 307 through the locking system 341 instead of the weight sensor.

The locking pin 343 is withdrawn from the opening 345 by the actuator 347 (FIG. 14B) in order measure the weight of the container. Once the locking pin 343 is withdrawn and the mounting plate is thereby released by the locking system, the weight sensor 305 bears the weight of the mounting plate 321, gripper assembly 303, and any object held by the gripper assembly. This can be done while the end effector 301 is held stationary with the container in a suspended position to avoid the influence accelerations might have on the weight measurement. If necessary, a dwell time can be used to allow the system to settle before the weight measurement is taken. The weight sensor sends a signal indicative of the load placed thereon. The weight of the container is determined by subtracting the weight of the mounting bracket 321 and gripper assembly 303.

Significantly, the end effector 303 allows the weight of the container to be measured without taking up any space on the work platform. This is important because the temperature of the work platform needs to be controlled to preserve the quality of frozen sample material on the work platform. In the case of handling frozen biological sample materials, the very low temperatures required result in a substantial cost when the area of the work platform that needs to be controlled is increased. A separate weigh station on the work platform would increase the amount of area that needs to be temperature controlled. By avoiding the need for a weight station on the platform, the end effector 303 allows weight measurements to be taken without increase the cost and difficulty associated with controlling the temperature of the work platform.

The end effector 301 can be used to measure the weight of containers at various times during the process of taking frozen sample cores from frozen sample materials in containers. For example, the end effector 301 can be used to measure the weight of a container as the container is moved to a drilling station before one or more sample cores are taken from the sample material in the container. The weight of the container before the frozen samples are taken can provide information about the level to which the container is filled with sample material. It can also provide information about how many frozen sample cores have already been taken from the container. The end effector 301 can weight the container after one or more frozen sample cores have been taken (e.g., while the end effector is used to replace the container in a storage rack on the work platform), in which case the difference between the weight of the container before drilling and after drilling provides information about the amount of material contained in the frozen sample cores taken from the container during the process. The end effector 303 can also be used to measure the weight of the container in which the frozen sample cores are placed (e.g., while the end effector is used to place the aliquot-containing container in a storage rack on the work platform). In this case, the difference between the weight of the aliquot-containing container and the tare weight of the container provides information about the amount of material contained in the aliquot-containing container.

In some of the methods described above, the processor uses only one aspect of the fill level detection system 131 to identify the position of the sample surface 129 (i.e., only the imaging system 161 or only the sensor 147 that detects contact between the end effector 101 and the sample surface 129. However, it is recognized that the processor may use more than one option for locating the frozen sample surface 129 concurrently in the same method to result in a more robust system. For example, the processor may use any combination of container weight, visual inspection of the sample by the vision system, and/or detecting when the end effector makes initial contact with the upper surface of the frozen sample to determine the level to which a sample container is filled with sample material. The weight measuring and fill level detecting capabilities of the end effector can thereby be used to produce a robust robotic system for taking frozen aliquots from frozen samples that ensures and verifies that each frozen aliquot contains at least a minimum amount of sample material.

When introducing elements of the present invention of the preferred embodiments thereof, the articles "a", "an", "the", and "said" are intended to mean that there are one or more of the elements. The terms "comprising", "including", and "having" are intended to be inclusive and mean that there may be additional elements other than the listed elements.

In view of the foregoing, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A robotic end effector for collecting frozen aliquots from an array of frozen samples, the frozen samples being contained in a plurality of containers, each frozen sample having a surface spaced from a bottom of the container, the robotic end effector comprising:

a coring bit for taking frozen sample cores from the frozen samples;

a frozen sample core extraction system adapted to move the coring bit relative to the frozen samples in a manner that extracts frozen sample cores from the frozen samples;

a fill level detection system adapted to detect the positions of the surfaces of the frozen samples; and a processor adapted to receive signals from the fill level detection system and use the signals and information concerning operation of the frozen sample core extraction system to determine at least one of the following: (a) the amount of material contained in a particular frozen sample; and (b) the number of frozen sample cores needed from a particular frozen sample to obtain a predetermined amount of material from that frozen sample.

2. A robotic end effector as set forth in claim 1 wherein the frozen sample core extraction system comprises a motor adapted to rotate the coring bit.

3. A robotic end effector as set forth in claim 1 wherein the coring bit has a longitudinal axis and the frozen sample core extraction system comprises a motor adapted to move the coring bit axially.

4. A robotic end effector as set forth in claim 3 further comprising an ejector adapted to eject a frozen sample core taken by the coring bit from the coring bit, the ejector being moveable between an extended position in which the ejector extends beyond a distal end of the coring bit and a retracted position in which the ejector does not extend beyond the distal end of the coring bit.

5. A robotic end effector as set forth in claim 4 wherein the fill level detection system comprises a sensor adapted to detect contact between the ejector and the surfaces of the frozen samples.

6. A robotic end effector as set forth in claim 5 wherein the sensor is adapted to detect a change in an electrical property, wherein the change is associated with contact between the ejector and the frozen sample.

7. A robotic end effector as set forth in claim 5 wherein the ejector is adapted to be moved from the extended position toward the retracted position by the frozen samples when the ejector is in the extended position and the robotic end effector is moved so the ejector contacts one of the frozen samples, the sensor comprising a sensor that detects movement of the ejector toward the retracted position.

8. A robotic end effector as set forth in claim 1 wherein the fill level detection system comprises a sensor adapted to detect contact between the robotic end effector and the surface of a frozen sample.

9. A robotic end effector as set forth in claim 1 wherein the fill level detection system comprises an imaging system, wherein the processor is adapted to move the imaging system relative to the surface of a frozen sample, determine when the imaging system is focused on the surface, and determine the position of the surface of said frozen sample using information about the position of the imaging system when it is focused on the surface of the frozen sample.

10. A fill level detection system for a frozen aliquotter system that automatically collects frozen aliquots from an array of frozen samples, the frozen samples being contained in a plurality of containers, each frozen sample having a surface spaced from a bottom of the container, the fill level detection system comprising a processor and at least one of the following:

(a) an imaging system and a system adapted to move the imaging system toward and away from one of the frozen samples, wherein the processor is adapted to determine when the imaging system is focused on the surface of said frozen sample and use information about the position of the imaging system when it is focused on the surface of said frozen sample to determine the position of the surface of the frozen sample;

(b) a probe, a system for moving the probe toward and away from the surface of one of the frozen samples, and a sensor adapted to detect contact between the surface of said frozen sample and the probe, wherein the processor is adapted to use a signal from the sensor and information about operation of the system for moving the probe to determine the position of the surface of said frozen sample; and (c) a robotic end effector comprising a gripper adapted to lift one of the containers and a sensor adapted to detect a weight of the lifted container by measuring a force exerted by the lifted container on the end effector, wherein the processor is adapted to use a signal from the sensor and information about the sample contained in the container to determine the position of the surface of said frozen sample, wherein the processor is adapted to determine a distance between the surface of said frozen sample and the bottom of the respective container.

11. A fill level detection system as set forth in claim 10 wherein the fill level detection system comprises a probe, a system for moving the probe toward and away from the surface of one of the frozen samples, a sensor adapted to detect contact between the surface of said frozen sample and the probe, and a processor adapted to use a signal from the sensor and information about operation of the system for moving the probe to determine the position of the surface of said frozen sample.

12. A fill level detection system as set forth in claim 11 wherein the probe comprises an ejector that is adapted to eject a frozen sample core from the coring bit.

13. A fill level detection system as set forth in claim 12 wherein the sensor comprises a sensor adapted to detect movement of the probe associated with contact between the probe and the surface of said frozen sample.

14. A fill level detection system as set forth in claim 12 wherein the sensor is adapted to detect a change in an electrical property, wherein the change is associated with contact between the probe and the surface of said frozen sample.

15. A fill level detection system as set forth in claim 10 wherein the fill level detection system comprises a robotic end effector comprising a gripper adapted to lift one of the containers and a sensor adapted to detect a weight of the lifted container by measuring a force exerted by the lifted container on the end effector, wherein the processor is adapted to use a signal from the sensor and information about the sample contained in the container to determine the position of the surface of said frozen sample.

16. A fill level detection system as set forth in claim 15 wherein the sensor is mounted on the end effector.

17. A fill level detection system as set forth in claim 16 further comprising a locking mechanism and first and second brackets, the second bracket being connected to the first bracket so the second bracket supports the weight of the first bracket, the locking system being operable to lock the first and second brackets into position relative to one another when the locking system is in a locked state, wherein the sensor is a strain gauge connecting the first bracket to the second bracket, the strain gauge being positioned so the stain gauge supports the weight of the first bracket when the locking system is in an unlocked state.

18. A fill level detection system as set forth in claim 17, wherein the strain gauge comprises a load cell.

19. An automated method of taking a frozen aliquot from a frozen sample contained in a container, the method comprising:

using a sensor to determine the position of a surface of the frozen sample that is spaced from a bottom of the container and output a signal indicative of the position of the surface to a processor;

robotically inserting the tip of a coring bit into the frozen sample under the guidance of the processor to the bottom of the container;

robotically withdrawing the coring bit from the frozen sample to obtain a frozen sample core, the frozen sample core forming at least part of the frozen aliquot; and ensuring that the frozen aliquot includes at least a predetermined minimum volume of sample material by using information about the position of the surface of the sample relative to the bottom of the container to determine whether or not the frozen aliquot contains at least the predetermined minimum volume of sample material.

20. An automated method as set forth in claim 19 further comprising repeating the inserting and withdrawing steps to obtain another frozen sample core from the frozen sample and adding said another frozen sample core to the frozen aliquot until the frozen aliquot contains at least the predetermined volume of sample material.

21. An automated method as set forth in claim 19 wherein finding the position of the surface of the frozen sample comprises robotically contacting the surface of the frozen sample with a probe and using a sensor to detect contact between the probe and the surface of the frozen sample.

22. An automated method as set forth in claim 21 further comprising using the probe to eject the frozen sample core from the coring bit.

23. An automated method as set forth in claim 19 wherein finding the position of the surface of the frozen sample comprises moving an imaging system relative to the sample and using the processor to determine when the imaging system is focused on the surface of the frozen sample.

24. An automated method as set forth in claim 19 further comprising placing the remaining frozen sample into a cryopreservation unit after taking the aliquot to store the remaining frozen sample for later use.

* * * * *